US008148130B2

(12) United States Patent
Alving et al.

(10) Patent No.: US 8,148,130 B2
(45) Date of Patent: Apr. 3, 2012

(54) T4 BACTERIOPHAGE BOUND TO A SUBSTRATE

(75) Inventors: Carl R. Alving, Bethesda, MD (US); Venigalla Rao, Washington, DC (US)

(73) Assignee: The Catholic University of America, Washington, DC (US)

( * ) Notice: Subject to any disclaimer, the term of this patent is extended or adjusted under 35 U.S.C. 154(b) by 72 days.

(21) Appl. No.: 12/039,803

(22) Filed: Feb. 29, 2008

(65) Prior Publication Data

US 2008/0274533 A1    Nov. 6, 2008

Related U.S. Application Data

(60) Provisional application No. 60/904,168, filed on Mar. 1, 2007.

(51) Int. Cl.
*C12N 7/01*     (2006.01)
*A61K 15/21*    (2006.01)
*A61K 9/127*    (2006.01)
*C12N 15/73*    (2006.01)

(52) U.S. Cl. .............. 435/235.1; 435/477; 424/1.21; 424/9.51; 424/417

(58) Field of Classification Search .................. None
See application file for complete search history.

(56) References Cited

U.S. PATENT DOCUMENTS

| | | | | |
|---|---|---|---|---|
| 4,416,872 | A | * 11/1983 | Alving et al. ..................... 514/8 |
| 5,952,454 | A | 9/1999 | Kovac et al. | |
| 2005/0226892 | A1 | 10/2005 | Rao | |

FOREIGN PATENT DOCUMENTS

WO    WO 2005/058006 A2    6/2005

OTHER PUBLICATIONS

Tanji et al. J. Biotech. 2004, vol. 114, No. 1-2, pp. 11-20.*
Furukawa et al. J. Bacteriology 1979, vol. 140, No. 3, pp. 1071-1080.*
Furukawa et al. (B) J. Bacteriology 1982, vol. 150, No. 2, pp. 916-924.*
Haensler et al. Glycoconjugate Journal 1991, vol. 8, pp. 116-124.*
Franz et al. ACTA VET.BRNO 1995, vol. 64, pp. 163-169.*
(X1 ): Glycolipid: defintion from Answers.com. p. 1-3, searched by Feb. 12, 2010.*
Olson et al. T4 strcutre, 2001, 2001, pp. 1-2.*
(V2): phosohatidlethanolamin in Wikipedia p. 1-3, searched on Feb. 12, 2010.*
(W2): AOCS Lipid Library, pp. 1-2 on liine searched on line Feb. 12, 2010.*
Kenneth T. Today'S Online Textbook of Bacgeriology, pp. 1-7, 2008.*
Furukawa et al. (A) (Journal of Bacteriology 1983, vol. 154, No. 2, pp. 938-945.*
Veterinary Dictionary published by Answer.com, searched by Oct. 23, 2010, pp. 1-3.*
Illustrated Dictionary of Immunology, edited by Cruse et al. 2003, pp. 38, 555.*
Henning et al. Journal of Bacteriology 1979, vol. 137, No. 1, pp. 664-666.*
Molecular Biology and Biotechnology, A Comprehensive Desk Reference, edited by Robert A Myers, 1995, page pp. 509-510 & 973.*
Seppala et al. Immunology 1984, vol. 53, pp. 827-836.*
Spherolplasts Definition from Answers.com, pp. 1-3, Oct. 23, 2010.*
FreeDictionary at http://medical-dictinary. thefreedictionary.com/glycoconjugate, Aug. 24, 2009, pp. 103.*
Shivachandra, S., et al., "In vitro binding of anthrax protective antigen on bacteriophage T4 capsid surface through Hoc-capsid interactions: a strategy for efficient display of large full-length proteins", *Virology*, Feb. 5;345(1):190-8 Epub Nov. 28, 2005 (2006).
Shivachandra, S.B., et al, Multicomponent anthrax toxin display and delivery using bacteriophage T4, *Vaccine*, 25:1225-35 (2007).
Shnaper, S., et al., "The C- and N-terminal Regions of Glycoprotein 41 Ectodomain Fuse Membranes Enriched and Not Enriched with Cholesterol, Respectively" *J. Biol. Chem.* 279:18526-18534 (2004).
Small, D.M., "The Physical States of Lipids: Solids, Mesomorphic States, and Liquids", "The Physical Chemistry of Lipids, from Alkanes to Phospholipds", *Handbook of Lipid Research*, vol. 4, Plenum, NY (1986) Chapter 3, pp. 43-87.
Studier, W., et al., "Use of T7 RNA polymerase to direct expression of cloned genes", *Methods in Enzymology*, 185, 61-89 (1990).
Su, D., et al., "The role of macrophages in the immunoadjuvant action of liposomes: effects of elimination of splenic macrophages on the immune response against intravenously injected liposome-associated albumin antigen," , *Immunology*, 66:466-470 (1989).
Verma, J.N., et al, "Adjuvant Effects of Liposomes Containing Lipid A: Enhancement of Liposomal Antigen Presentation and Recruitment of Macrophages," *Infection. Immunity* 60:2438-2444 (1992).
Verma, et al., "Phagocytosis of liposomes by macrophages: intracellular fate of liposomal malaria antigen," *Biochim. Biophys. Acta.*, Jul. 22, 1991; 1066(2): 229-38. Abstract Only.
Wassef, et al., "Lipsomes as Carriers for Vaccines," *Immunomethods* 4, 217-222 (1994).
Yu, F., et al, "Roles of Lipopolysaccharide and Outer Membrane Protein OmpC of *Escherichia coli* K-12 in the Receptor Function for Bacteriophage T4," *J. Bacteriol.*, 151(2):718-722 (1982).
International Search Report and Written Opinion for PCT/US08/55422 mailed Aug. 11, 2008.
Li, Q., et al., "Bacteriophage T4 Capsid: A Unique Platform for Efficient Surface Assembly of Macromolecular Complexes" *J. Mol. Biol.* 363:577-578 (2006).
Li, Q., et al., "Assembly of the Small Outer Capsid Protein, Soc, on Bacteriophage T4: A Novel System for High Density Display of Multiple Large Anthrax Toxins and Foreign Proteins on Phage Capsid" in *J. Mol.Biol.*, 370:1006-1019 (2007).
March et al., "Genetic immunistion against hepatitis B using whole bacteriophage λ particles," *Vaccine*, 22 1666-1671 (2004).
Mooney, D.T., et al., *J. Virol.*, 61, 2828-2834 (1987)—[For use in the in vitro system of the present invention, the hoc and/or soc T4 bacteriophage particles need to be isolated and should be substantially pure. One may isolate these T4 bacteriophage particles by any means known].
Nourez, M., et al., "Designing a polyvalent inhibitor of anthrax toxin" *Nature Biotechnology*, 19, 958-961 (2001).
Palmer, D.R., et al., "Restricted replication and lysosomal trafficking of Yellow Fever 17D vaccine virus in human dendritic cells", *J. Gen. Virol.*, Jan.;88(pt1):148-56 (2007).

(Continued)

*Primary Examiner* — Bao Li
(74) *Attorney, Agent, or Firm* — Vedder Price P.C.; Ajay A. Jagtiani

(57) ABSTRACT

T4 bacteriophages are bound to substrates such as liposomes using a binder.

19 Claims, 11 Drawing Sheets

OTHER PUBLICATIONS

Peachman, K.K., et al., "Human Dendritic Cells and Macrophages Exhibit Different Intracellular Processing Pathways for Soluble and Liposome-Encapsulated Antigens", *Immunobiology*, 210:321-333 (2005).

Prehm, P., et al. "On a Bacteriophage T3 and T4 Receptor within the Cell Wall Lipopolysaccharide of *Escherichia coli* B.," *B.J. Mol. Biol.*, 101:277-281 (1976).

Rao, M., et al, "Immunostimulatory CpG motifs induce CTL responses to HIV type I oligomeric gp140 envelope protein", *Immunology and Cell Biology*, 82: 523-530 (2004).

Rao, V.B., et al., "DNA packaging of Bacteriophage T4 Proheads in vitro: Evidence that Prohead Expansion is not Coupled to DNA Packaging", *J. Mol. Biol.*, 185: 565-578 (1985).

Rao, V.B., et al., "The N-Terminal ATPase Site in the Large Terminase Protein gp17 is Critically Required for DNA Packaging in Bacteriophage T4", *J. Mol. Biol.*, 314: 411-421 (2001).

Ren, Z.J., et al., "Phage display of intact domains at high copy number: a system based on SOCX, the small outer capsid protein of bacteriophage T4" *Protein Science* 5:1833-43 (1996).

Sanchez-Martines, S., et al., "Specific phospholipid recognition by human immunodeficiency virus type-1 neutralizing anti-gp41 antibody", *FEBS Letters*, 508:2395-2399 (2006).

Sathaliyawala, T., et al., Assembly of Human Immunodeficiency Virus (HIV) antigens on Bacteriophage T4: a Novel In Vitro Approach to Construct Multicomponent HIV Vaccines, *J. Virology*, 80: 7688-7698 (2006).

Alving, C.R, et al., Liposomes as carriers of peptide antigens: Induction of antibodies and cytotoxic T lymphocytes to conjugated and unconjugated peptides *Immunol. Rev.*, 145:5-31 (1995)—Abstract Only.

Alving, C.R., et al., "Preparations and use of liposomes in immunological studies", *Liposome Technology:* G. Gregoriadis, ed., CRC Press Inc., Boca Raton, Fl, vol. 3, p. 317-343 (1993).

Alving, C.R., et al."Design and selection of vaccine adjuvants: animal models and human trials," *Vaccine*,20:S56-S64 (2002).

Alving, C.R., et al., "Novel Vaccines and Adjuvants: Mechanisms of Acton, Cytotoxic T Lymphocytes Induced by Liposomal antigens: Mechanisms of Immunological Presentation," *AIDS Research. And Human Retroviruses*,vol. 10, Supplement 2, (1994), Mary Ann Liebert, Inc., Publishers.

Black, L.W. et al., "Mechanistic coupling of bacteriophage T4 DNA packaging to components of the replication-dependent late transcription machinery" *J. Biol. Chem.* 281:25635-43 (2006).

Brown, B.K., Darden, J.M., Tovanabutra, S., Oblander, T., Frost, J., Sanders-Buell, E., deSouza, M.S., Birx, D.L., McCutchan, F.E., and Polonis, V.R., "Biologic and genetic characterization f a panel of 60 human immunodeficiency virus type 1 isolate, representing clades A, B, C, D, CRF01_AE, and CRF02_AG, for the development and assessment of candidate vaccines", *Journal of Virology*, 79:6089-6101 (2005).

Brown, B.K., Karasavvas, N., Beck, Z., Matyas, G.R., Birx, D.L., Polonis, V.R., and Alving, C.R., "Monoclonal antibodies to phosphatidylinositol phosphage neutralize human immunodeficiency virus type 1: role of phosphate-binding subsites", *Journal of Virology*, 81:2087-2091 (2007).

Clark et al., "Bacteriophage-mediated nucleic acid immunization," FEMS Immunology and Medical Microbiology, 40, 21-26 (2004).

Dawes, J., "Characterisation of the bacteriophage T4 receptor site," *Nature*, 256:127-128 (1975).

Fokine, et al., "Cyro-electron microscopy study of bacteriophage T4 displaying anthrax toxin proteins", *Virology*, 367:422-427 (2007).

Fries, et al., "Liposomal malaria vaccine inhumans: A safe and potent adjuvant strategy," *Proc. Natl Aad. Sci.*(*USA*), 89:358-362 (1992).

Gluck, R., "Adjuvant activity of immunopotentiating reconstituted influenza virosomes (IRIVs)" *Vaccine*, 17:1782-1787 (1999).

Horton, R.M., et al., "Engineering hybrid genes without the use of restriction enzymes: gene splicing by overlap extension" *Gene*, 77, 61-68 (1989).

Jiang, J., et al.. "Display of a PorA Peptide form *Neisseria meningitides* on the Bacteriophage T4 Capsid Surface" *Infection and Immunity* 65: 4770-4777 (1997).

Kondabagil, K.R., Zhang, et al., "The DNA translocating ATPase of bacteriophage T4 packaging motor", *J. Mol. Biol.*, 363:786-799 (2006).

Kuebler, et al., "Functional Analysis of the DNA-Packaging/Terminase Protein gp17 from Bacteriophage T4", *J. Mol. Biol.*, 281:803-814 (1998).

Kung, et al., "Synthesis of carboxyacyl derivatives of phosphatidyletanolamine and use as an efficient method for conjugation of protein to liposomes" *Biochimica et. Biophysica. Acta* 862:435-439 (1986).

Leffers, et al., "A discontinuous headful packaging model for packaging less than headful length DNA molecules by bacteriophage T4", *J. Miol. Biol.*, 258:839-850, (1996).

Leiman, et al., "Structure and morphogenesis of bacteriophage T4" *Cell. Mol. Life Sci.*, 60(11):2356-2370 (2003).

\* cited by examiner

T4 BACTERIOPHAGE BOUND TO A SUBSTRATE

CROSS-REFERENCE TO RELATED APPLICATIONS

This application claims the priority of U.S. Provisional patent Application No. 60/904,168 entitled "Liposome-Bacteriophage Complex As Vaccine Adjuvant;" filed Mar. 1, 2007, the entire disclosure and contents of which is hereby incorporated by reference.

GOVERNMENT INTEREST STATEMENT

The United States Government has rights in this invention pursuant to Contract No. U01-AI056443-01 between Walter Reed Army Institute of Research and The Catholic University of America through a Cooperative Research Agreement.

STATEMENT OF JOINT RESEARCH AGREEMENT

In compliance with 37 C.F.R. §1.71(g) (1), disclosure is herein made that the claimed invention was made pursuant to a Joint Research Agreement as defined in 35 U.S.C. 103 (c) (3), that was in effect on or before the date the claimed invention was made, and as a result of activities undertaken within the scope of the Joint Research Agreement, by or on the behalf of The Catholic University of America and Walter Reed Army Institute of Research.

BACKGROUND

1. Field of the Invention

The present invention relates generally to antigen carriers.

2. Related Art

In the course of developing optimal constructs for vaccine formulation, it has been observed that vaccine formulations can be improved by utilizing liposomes to carry the antigen, or the adjuvant or both, rather than by using just a water-soluble composition. However, despite their many advantages, liposomes are difficult to manufacture and may have limited commercial potential for many vaccines.

SUMMARY

According to one broad aspect, the present invention provides composition comprising: a substrate; and one or more T4 bacteriophage components that are each bound to the substrate by a glucoconjugate.

According to a second broad aspect, the present invention provides a method comprising the following steps: (a) providing a substrate having one or more glucoconjugates bound thereto; and (b) binding each of one or more T4 bacteriophage components to a respective glucoconjugate of the one or more glucoconjugates.

According to a third broad aspect, the present invention provides a composition comprising: a liposome; and one or more T4 bacteriophage components bound to the liposome by a T4-liposome binder.

According to a fourth broad aspect, the present invention provides a method comprising the following steps: (a) providing a liposome having one or more T4-liposome binders bound thereto; and (b) binding each of one or more T4 bacteriophage components to a respective T4-liposome binder of the one or more T4-liposome binders.

According to a fifth broad aspect, the present invention provides a method comprising the following steps: (a) providing one or more T4 bacteriophage components each having one or more ligands bound thereto; and (b) binding each of one or more T4 bacteriophage components to a liposome having a receptor bound thereto, wherein the ligand and receptor comprises a ligand-receptor binder system.

BRIEF DESCRIPTION OF THE DRAWINGS

The invention will be described in conjunction with the accompanying drawings, in which.

DETAILED DESCRIPTION

Figure 1:
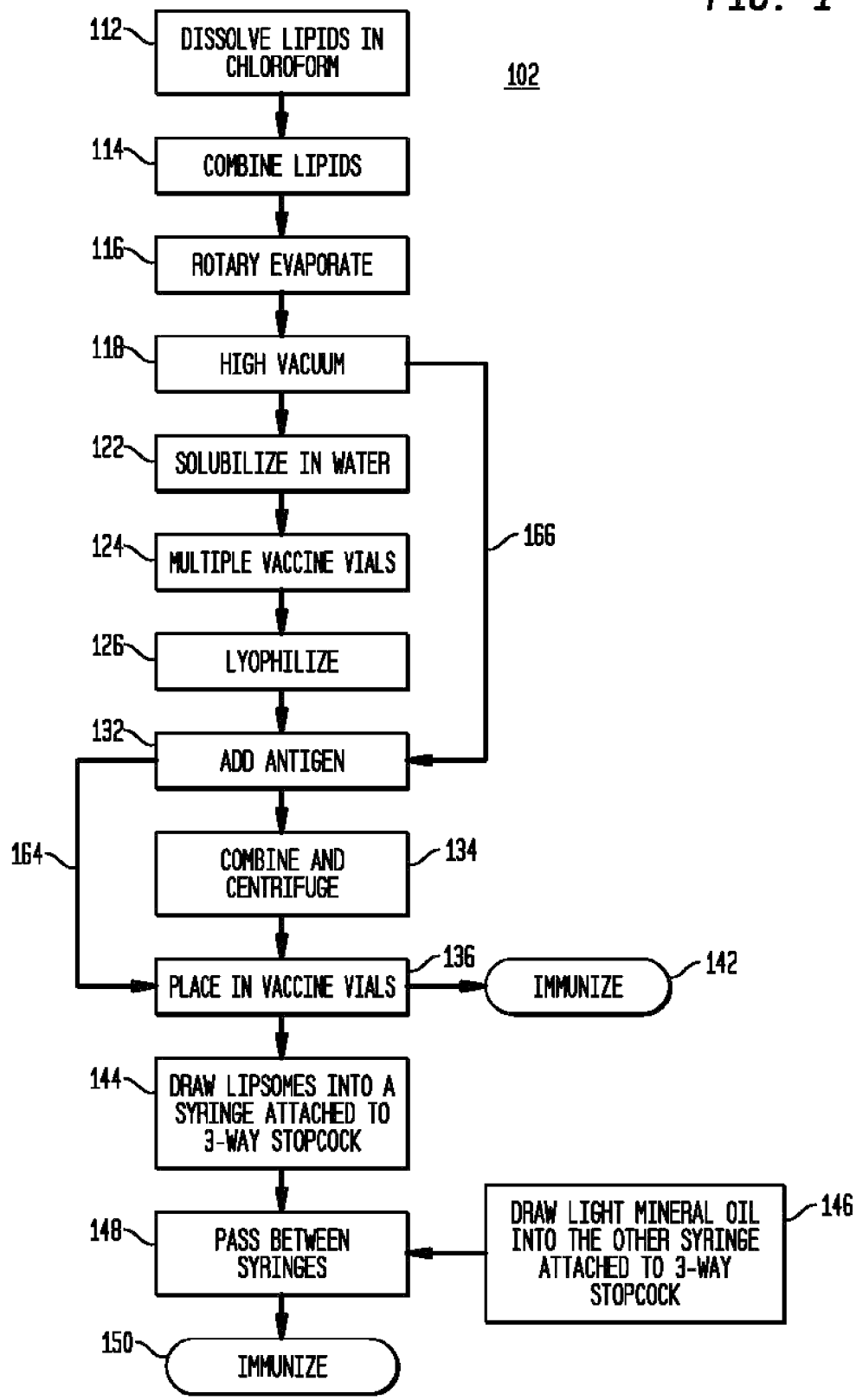
FIG. 1 is a flow chart showing a typical scheme for manufacturing of large multilamellar liposomes that are used directly for immunization or that can be incorporated into an oil-in-water emulsion.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For purposes of the present invention, the term, "adjuvancy" refers to the ability of an agent to enhance and/or promote the immune response of animal to a particular antigen.

For the purposes of the present invention, the term "adjuvant" or "vaccine adjuvant" refers to any substance or strategy that improves the adaptive immune response or that stimulates the innate immune system to induce desired effectors or mediators. New forms of vaccine adjuvants that have been proposed for various vaccines feature oil-based emulsions; bacterial products, such as lipid A, heat-labile *Escherichia coli* enterotoxin, or CpG nucleotides; viral products, such as virus-like particles; plant products, such as saponin derivatives; biodegradable particles, such as liposomes; molecular adjuvants; and synthetic adjuvants. An adjuvant may also be thought of as a substance or material for enhancing and/or that potentiates an immune response when used in conjunction with antigens and/or immunogens. Adjuvants may also be used to elicit immune response sooner, or a greater response, or with less antigen or immunogen. An adjuvant, such as lipid A may added to an already formed substrate, such as a liposome, or is the addition of the adjuvant, such as lipid A, part of forming the substrate, such as a liposome.

For the purposes of the present invention, the term "antigen" refers to a substance or material that is recognized specifically by antibody and/or combines with an antibody. Examples of antigens include: virus particles or organisms such as HIV, anthrax, plague, influenza, etc., or derivatives of the virus particles or organisms such as HIV gp120, anthrax protective antigen, etc.

For the purposes of the present invention, the term "antigen presenting cell (APC)" refers to a cell that presents an antigen. Examples of such cells include dendritic cells, macrophages, etc.

For the purposes of the present invention, the term "bacteriophage component" refers to bacteriophages and bacteriophage derivatives, including bacteriophages and bacteriophage derivatives having antigens, fusion proteins and other types of molecules attached thereto. For example, the term "T4 bacteriophage component" refers to T4 bacteriophages and T4 bacteriophage derivatives.

For the purposes of the present invention, the term "bacteriophage derivative" refers to any structure including at least part of the protein coat of a bacteriophage. An example of a bacteriophage derivative is where foreign DNA is packaged into a customized bacteriophage's genome as described, for example, in Jiang, J., Abu-Shilbayeh, L. and Rao, V. B., "Display of a PorA Peptide form *Neisseria meningitidis* on the Bacteriophage T4 Capsid surface" in *Infection and Immunity* 65:4770-4777 (1997), Clark et al., *FEMS Immunology and Medical Microbiology*, 40, 21-26 (2004) and March et al., *Vaccine*, 22, 1666-1671 (2004), the entire contents and disclosures of which are hereby incorporated by reference. Another example of a bacteriophage derivative is a bacteriophage capsid. Another example of a bacteriophage derivative is a bacteriophage tail. In one embodiment of the present invention, foreign DNA may be loaded into empty T4 capsids using the methods described in Kondabagil, K. R., Zhang, Z. B. and Rao, V. B., "The DNA translocating ATPase Of bacteriophage T4 packaging motor" in *J. Mol. Biol.*, 363: 786-799 (2006), the entire contents and disclosure of which is hereby incorporated by reference.

For the purposes of the present invention the terms "bind", "binding" and "bound" refer to any type of chemical or physical binding including: covalent binding, hydrogen binding, etc.

For the purposes of the present invention, the term "dosage form" refers to a pharmaceutical delivery of any pharmaceutically active compound including an antigen via any route of administration, but preferably including subcutaneous, topical, intramuscular, intradermic, intramammary, intraperitoneal and intra-ocular. The term "dosage form" in the immunogenic or vaccine aspect of the present invention will be understood to mean any pharmaceutical form of administering a vaccine including oral, subcutaneous, intramuscular, intra-ocular, administration and utilizing vaccines in live, attenuated or synthetic or partial forms along with adjuvants and optionally immunomodulators such as cytokines. The combinations of the foregoing elements are prepared so that the immunogenic dosage form is adapted to produce an immune response in the subject animal including a human as easily and effectively as possible. Dosage forms of the present invention also include unit dosage forms, i.e., dosage forms which are administered in individual units at a dosage effective for therapy or to elicit an immunological response.

For the purposes of the present invention, the term "epitope" refers to the smallest part of an antigen moiety recognizable by the combining site of an immunoglobulin.

For the purposes of the present invention, the term "extended elaboration" refers to the release of therapeutic agents from liposomal encapsulation over a period in excess of what would normally occur without the presence of stable liposomes and generally in about 24 hours and in some embodiments as long as about 2 to 3 weeks.

For the purposes of the present invention, the term "glucoconjugate" refers to a glycoconjugate which includes one or more glucose units available for binding a bacteriophage to a substrate. An example of a glucoconjuage is glucosyl ceramide (GC). Other examples of glucoconjugates suitable for use in various embodiments of the present invention are described below. In the present invention, glucoconjugates may be used as binders to bind a T4 bacteriophage to a substrate, such as a liposome.

For the purposes of the present invention, the term "glycoconjugate" refers to the conventional meaning of the term glycoconjugate i.e. a carbohydrate that is covalently linked with one or more chemical species. There are many types of glycoconjugates including: glycoproteins, glycopeptides, peptidoglycans, glycolipids, etc.

For the purposes of the present invention, the term "immune response" refers to a specific response of the immune system of an animal to antigen or immunogen. Immune response may include the production of antibodies and cellular immunity.

For the purposes of the present invention, the term "immunity" refers to a state of resistance of a subject animal including a human to an infecting organism or substance. It will be understood that an infecting organism or substance is defined broadly and includes parasites, toxic substances, cancer cells and other cells as well as bacteria and viruses. A "Therapeutically Effective Immunization Course" (see below for definition) will produce the immune response.

For the purposes of the present invention, the term "immunization conditions" refers to factors which affect an immune response including the amount and kind of immunogen or adjuvant delivered to a subject animal including a human, method of delivery, number of inoculations, interval of inoculations, the type of subject animal and its condition. "Vaccine" refers to pharmaceutical formulations able to induce immunity.

For the purposes of the present invention, the term "immunization dose" refers to the amount of antigen or immunogen needed to precipitate an immune response. This amount will vary with the presence and effectiveness of various adjuvants. This amount will vary with the animal and the antigen, immunogen and/or adjuvant but will generally be between about 0.1 µg/ml or less to about 100 µg per inoculation. The immunization dose is easily determined by methods well known to those skilled in the art, such as by conducting statistically valid host animal immunization and challenge studies as described, for example, Manual of Clinical Immunology, H. R. Rose and H. Friedman, American Society for Microbiology, Washington, D.C. (1980), the entire contents and disclosure of which is hereby incorporated by reference. In some instances, several immunization doses including booster doses may administered to provide immunity, and, for the purposes of the present invention such a course of treatment is collectively referred to as "Therapeutically Effective Immunization Course".

For the purposes of the present invention, the term "immunogen" refers to a substance or material (including antigens) that is able to induce an immune response alone or in conjunction with an adjuvant. Both natural and synthetic substances may be immunogens. An immunogen is generally be a protein, peptide, polysaccharide, nucleoprotein, lipoprotein, synthetic polypeptide, or hapten linked to a protein, peptide, polysaccharide, nucleoprotein, lipoprotein or synthetic polypeptide or other bacterial, viral or protozoal fractions. It will be understood that "immunogen" includes substances (e.g., small peptides) which do not generate an immune response (or generate only a therapeutically ineffective immune response) unless associated with an adjuvant. For the purposes of the present invention, such immunogens are referred to as "adjuvant-obligatory" immunogens.

For the purposes of the present invention, the term "immunogenic amount" is an amount of an infectious pathogen antigen preparation of interest or amount of a biological toxin that elicits a clinically detectable protective response in an animal.

For the purposes of the present invention, the term "labile peptide-like therapeutic agents" refers to the propensity for destruction or denaturation of the therapeutic agent in an animal by reactions other than the intended therapeutic reactions.

For the purposes of the present invention, the term "lipid bilayer membrane" refers to a type of double layer smectic mesophase in which the polar groups of the parallel array of lipids of each monolayer of lipids are oriented toward the aqueous phase and the nonpolar groups (such as fatty acyl groups) of each monolayer are oriented toward each other in the center of the bilayer. Highly hydrophobic compounds such as triglycerides, sterols such as cholesterol which may be incorporated into the bilayer in addition to the lipids that form the bilayer. Liposomes often contain lipid bilayers, as do plasma membranes of cells.

For the purposes of the present invention, the term "ligand-receptor binder system" refers to a T4-liposome binder comprising two molecules: a ligand displayed on the bacteriophage component and a receptor displayed on the liposome. Examples of ligand-receptor binder systems include: T4-Hoc fusion proteins or T4-Soc fusions proteins including the MPER region of HIV gp41 as the ligand and gp120 as the receptor, T4-Hoc fusion proteins or T4-Soc fusions proteins including gp120 as the ligand and CD4 as the receptor, T4-Hoc fusion proteins or T4-soc fusions proteins including anthrax protective antigen as the ligand and anthrax toxin as the receptor, etc.

For the purposes of the present invention, the term "lipid structure" refers to all organized lipid structures, or domains, and all solid phase, mesomorphic, crystalline, liquid crystalline, and liquid lipid structures, etc.: Lipid structure include all of the multiple organized physical states of lipids, as taught by Small, D. M., in "The physical states of lipids: solids, mesomorphic states, and liquids" in "The Physical Chemistry of Lipids, From Alkanes to Phospholipids" Handbook of Lipid Research, Vol, 4, Plenum, N.Y., 1986, Chapter 3, pp. 43-87, the entire contents and disclosure of which is hereby incorporated by reference. The terms "lipid structure" and "physical state of a lipid" are equivalent concepts for the purposes of the present invention. Thus, the term "solid phase lipid structure" is interchangeable with "mesomorphic states", "liquid lipids", "organized lipid structures" "domains", "crystalline lipid structures", liquid crystal lipid structures", and "liquid lipid structures".

For the purposes of the present invention, the term "lipid" refers to any molecule of intermediate molecular weight (between 100 and 5000) that contains a substantial portion of aliphatic or aromatic hydrocarbon. Examples of lipids include fatty acids, fats, oils, waxes, hydrocarbons, steroids, sterols, fat-soluble vitamins (such as vitamins A, D, E and K), monoglycerides, soaps, detergents, etc. and more complex molecules, such as triacylglycerols, phospholipids, gangliosides, and lipopolysaccharides, etc. Lipids further include highly hydrophobic compounds such as triglycerides, sterols such as cholesterol. Specific lipids that may be used in the present invention include phospholipids such as phosphatidylcholine (PC), phosphatidylethanolamine (PE), distearoyl phosphatidylcholine (DSPC), phosphatidylserine (PS), phosphatidylglycerol (PG), phosphatidic acid (PA), phosphatidylinositol (PI), sphingomyelin (SPM), and the like, alone or in combination. The phospholipids can be synthetic or derived from natural sources such as egg or soy. Some synthetic phospholipids are dimyristoylphosphatidylcholine (DMPC) and dimyristoylphosphatidylglycerol (DMPG). For a further description of lipids useful in the present invention, see the definition of "lipid" in Small, D. M., "The Physical Chemistry of Lipids, From Alkanes to Phospholipids" Handbook of Lipid Research, Vol, 4, Plenum, N.Y., 1986, p. 1, the entire contents and disclosure of which is hereby incorporated by reference.

For the purposes of the present invention, the term "liposome" refers to a vesicle composed of a bilayer membrane, such as a bilayer membrane composed of a phospholipid and a cholesterol bilayer. Liposomes may also contain other steroid components such as polyethylene glycol derivatives of cholesterol (PEG-cholesterols), coprostanol, cholestanol, or cholestane, and combinations of PC and cholesterol. Liposomes may also contain glycolipids. A liposome may consist of smectic mesophases, and may consist or either phospholipid or nonphospholipid smectic mesophases.

For the purposes of the present invention, the term "native state configuration" refers to organization of a moiety, such as a peptide, as it is configured when present in situ, i.e, in the native state, to be distinguished from non-native state configuration (denatured) wherein the moiety may be altered as to bioactivity or immunoreactivity.

For the purposes of the present invention, the term "particle" refers to any substrate having a minimum diameter of 0.01 microns and a maximum diameter of no greater than 1000 microns.

For the purposes of the present invention, the term "peptide-like" refers to short chain peptides as well as proteins, lipoproteins and glycoproteins, but will also, for convenience, include non-proteinaceous molecules for example, amino acid containing molecules. In certain embodiments, the peptide-like therapeutic agent may additionally comprise vitamins, steroids, azidothymidine, and free primaquine in addition to other agents. One useful class of peptides is immunomodulators such as interleukins, colony stimulating factors and interferons. Another useful class of proteins is antigens and immunogens such as are used in vaccines.

For the purposes of the present invention, the term "priming" refers to the stimulation of a primary (as opposed to a secondary or later) response by an animal to an immunogen.

The primary response is characterized by the manufacture by the animal of antibody to the immunogen, and ideally by the generation of a population of B-lymphocytes that respond to secondary or later immunogenic challenge—even absent adjuvant—with a rapid and substantive production of antibodies. Based upon such response 1, 2, 3 or more booster doses of immunogen absent adjuvant will generate a therapeutically effective immune response to the immunogen.

For the purposes of the present invention, the term "self-assembly" refers to the spontaneous binding of bacteriophage components to a substrate. In some embodiments, self-assembly requires the presence of a solvent or suspension fluid such as water. For example the spontaneous binding of bacteriophage particles on the surface of the liposomes including a glucoconjugate in an aqueous medium or binding of bacteriophages to liposomes caused by the addition of an aqueous medium to a mixture of dried bacteriophages and liposomes including glucoconjugates would both be self-assembly processes.

For the purposes of the present invention, the term "smectic mesophase" refers to molecules in single or double layers, normal or tilted to the plane of the layer, and with frozen or melted aliphatic chains. When a given molecule is heated, instead of melting directly into an isotropic liquid, it may instead pass through intermediate states called mesophases or liquid crystals, characterized by residual order in some directions but by lack of order in others. In general, the molecules of liquid crystals are somewhat longer than they are wide and have a polar or aromatic part somewhere along the length of the molecule. The molecular shape and the polar-polar, or aromatic, interaction permit the molecules to align in partially ordered arrays. These structures characteristically occur in molecules that possess a polar group at one end. Liquid crystals with long-range order in the direction of the long axis of the molecule are called smectic, layered, or lamellar liquid crystals. In the smectic states the molecules may be in single or double layers, normal or tilted to the plane of the layer, and with frozen or melted aliphatic chains. For a further description of "smectic mesophase," see Small, D. M., in "The Physical Chemistry of Lipids, From Alkanes to Phospholipids" Handbook of Lipid Research, Vol, 4, Plenum, N.Y., 1986, pp. 49-50, the entire contents and disclosure of which is incorporated by reference.

For the purposes of the present invention, the term "stabile lipid" refers to lipids which are resistant to oxidative catabolism initiated by changes in pH, temperature, oxygen free radicals (e.g., such as those produced by infiltrating immune cells during inflammatory reaction) or other stress of the physiological environment. It is to be understood that stabile is a property in the nature of a continuum whereby normal lipid rigidity is modified by a stabilizing process such as hydrogenation. Thus a stabile lipid is a lipid resistant to oxidative catabolism initiated by changes in pH, as well as resistant to temperature, oxygen free radicals or other stresses of the physiological environment and is not rapidly deconstructed at common physiologic pH ranges presented in the in vivo environment of use. Stabile lipids, when organized into liposomes, will maintain structural integrity for an extended period of time in the physiological environment after parenteral administration, particularly as compared to other liposomes.

For the purposes of the present invention, the term "structural integrity of liposomes" refers to the substantial maintenance of the pharmaceutical activity of the encapsulated substance during a period of extended elaboration. This structural integrity is presumed to arise from the persistence of the bilayer arrangement of the lipid material comprising the liposomes and the concomitant substantial maintenance of an entrapped aqueous phase for the period of extended elaboration. Structural integrity may be imparted by forming liposomes from combinations of lipids comprising sufficient stabile lipid to maintain the required structure when challenged by the physiological conditions present in the subject animal.

For the purposes of the present invention, the term "T4-liposome binder" refers to any molecule or combination of molecules that may be used to bind a T4-bacteriophage component to a liposome. In some embodiments, the T4-liposome binder may be bound to the liposome allowing a T4 bacteriophage component to bind to the liposome through the T4-liposome binder. For example, the T4-liposome binder glucosyl ceramide or cholest-5-en-3B (dithiopyridine) (PDS-cholesterol), may be bound to a liposome and then a T4 bacteriophage may be bound to the liposome through the binder. In other embodiments, the T4-liposome binder may be a ligand-receptor binder system and comprise two molecules: one molecule bound to the bacteriophage and one molecule bound to the liposome.

For the purposes of the present invention, the term "vaccine" refers to a formulation that comprises a liposome or liposomes and an antigenic species capable of provoking an immune response in an animal.

DESCRIPTION

Liposomal vesicles can be safely administered to humans for vaccines as described for example in Gluck, R., *Vaccine*, 17:1782-1787 (1999), the entire contents and disclosure of which is hereby incorporated by reference. The use of liposomal vesicles as vaccines takes advantage of the fact that particulate materials are readily taken up by phagocytic cells, such as dendritic cells or macrophages, and these cells then serve as antigen presenting cells (APCs) for mounting a specific immune response to the antigen associated with the particle, as described in Verma, J. N., Rao, M., Amselem, S., Krzych, U., Alving, C. R., Green, S. J., Wassef, N. M., *Infect. Immun.*, 60:2438-2444 (1992) and in Peachman, K. K., Rao, M., Alving, C. R., Palmer, D. R., Sun, W., Rothwell, S. W., *Immunobiology*, 210:321-333 (2005), and the entire contents and disclosures of these articles is hereby incorporated by reference. Because of this mechanism of interacting with the immune system, particulate materials can sometimes have greater efficiency or potency for inducing immune responses superior to that of soluble materials, as soluble materials are not as avidly taken up by APCs.

However, it is known that simple uptake of a particular antigen by antigen presenting cells (APCs) may not always give the strongest possible immune response, and adjuvants are often required for enhancement of the immune response or for channeling the immune response in a particular direction, as described in Alving, C. R., *Vaccine*, 20:S56-S64 (2002), the entire contents and disclosure of which is hereby incorporated by reference. An example of liposome-associated lipid A serving as both an intracellular and extracellular adjuvant has been described in Verma, J. N., Rao, M., Amselem, S., Krzych, U., Alving, C. R., Green, S. J., Wassef, N. M., *Infect. Immun.*, 60:2438-2444 (1992), the entire contents and disclosure of which is hereby incorporated by reference.

Liposomal vesicles are highly versatile and can be prepared either as nanoparticles or as mixtures of varying sizes. Antigens can be reconstituted within the lipid bilayers of the liposomes, either encapsulated within the internal aqueous spaces; or covalently attached to the outer surface. For example, liposomes or liposomes containing attached or encapsulated antigen and also containing lipid A as an adjuvant that exhibit superior immunogenicity have been described in Alving, C. R., Koulchin, V., Glenn, G. M., and Rao, M., *Immunol. Rev.,* 145:5-31 (1995), the entire contents and disclosure of which is hereby incorporated by reference.

One of the attractive features for using liposomes as vehicles for the delivery of antigens is an observed rapid uptake of liposomes by macrophages and immature dendritic cells as described in Su, D., Van Rooijen, N., *Immunology,* 66:466-470 (1989), in Verma, J. N., Wassef, N. M., Wirtz, R. A., Atkinson, C. T., Aikawa, M., Loomis, L. D., Alving, C. R., *Biochim. Biophys. Acta.,* 1066:229-308 (1991) and in Verma, J. N., Rao, M., Amselem, S., Krzych, U., Alving, C. R., Green, S. J., Wassef, N. M., *Infect. Immun.,* 60:2438-2444 (1992), and the entire contents and disclosures of these articles are hereby incorporated by reference.

Liposomal antigens have the added potential of being able to simultaneously gain entry into both the conventional MHC class I and the MHC class II pathways. This characteristic presents the advantage of inducing both antibody and cellular immune responses as described in Alving, C. R., Koulchin, V., Glenn, G. M., and Rao, M., *Immunol. Rev.,* 145:5-31 (1995) and in Alving, C. R., Wassef, N. M., *IDS Res. and Human Retrovir.,* 10; S91 (1994), the entire contents and disclosure of which are hereby incorporated by reference. Liposomes have also proven to be an efficient delivery system for entry of exogenous protein antigens into the MHC class I pathway due to their particulate nature, as described in Alving, C. R., Wassef, N. M., *IDS Res. and Human Retrovir.,* 10; S91 (1994), the entire contents and disclosure of which is hereby incorporated by reference. All of these properties lead to the ability of vaccines employing liposomes as an adjuvant to provide for a strong induction of desired immunological responses.

However, despite their many advantages, liposomes are difficult to manufacture and may have limited potential for commercial development for vaccines. Self-assembling formulations of liposomes, termed WRAIR liposomes, have been invented at the Walter Reed Army Institute of Research (WRAIR). WRAIR liposomes are composed of dimyristoyl phosphatidylcholine, dimyristoyl phosphatidylglycerol, cholesterol, and lipid A and are described in Wassef, N. M., Alving, C. R., Richards, R. L. *Immuno. Methods.,* 4; 217-222 (1994), the entire contents and disclosure of which is hereby incorporated by reference. WRAIR liposomes have greater manufacturing reproducibility than traditional liposomes and can be made under GMP (Good Manufacturing Practice) conditions. Nevertheless, the best liposomes for vaccines are typically large multilamellar vesicles, even up to 50 to 100 microns in diameter that can be easily ingested by phagoyctic cells. Because of this, such liposomes cannot undergo a final filtration and must be manufacture under sterile conditions. A typical flow chart showing a scheme for the manufacture of large multilamellar liposomes that are used directly for immunization or that can be incorporated into an oil-in-water elusion is provided in FIG. 1.

In scheme 102, the lipids begin as a dried film or as a lyopilized lipids. The lipids are dissolved in chloroform in step 112 and are combined in step 114. The combined lipids are then subject to rotary evaporation in step 116 and high vacuum in step 118 to produce a dried film. The dried film is solubilized in water in step 122 and added to multiple vaccine vials in step 124. The solubilized lipids are then lyophilized in step 126 to form a solubilized lyophilized lipid composition. An antigen is then added to the lipid composition in step 132.

The lipid composition and antigen are combined and centrifuged in step 134 and placed in vaccine vials in step 136. The product in the vaccine vials may be used to immunize directly as shown by step 142. Alternatively, the liposomes in the vaccine vials may be drawn into a syringe attached to a 3-way stopcock in step 144, a light mineral oil may be drawn into the other syringe attached to the 3-way stopcock in step 146 and the light mineral oil and liposomes mixed in step 148 by passing the liposomes and light mineral oil between the syringes. The resulting composition may used to immunize as shown in step 150.

In an alternative scheme, steps 122, 124 and 126 may be skipped, as shown by arrow 162, and the antigen may be added directly to the dried film in step 132.

In another alternative scheme, combining and centrifuging step 134 may be omitted as shown by arrow 164.

In the scheme of FIG. 1 the lipids begin as a dried film or a lyophilized powder. The liposomes are subsequently formed as an aqueous suspension of large vesicles by adding the antigen dissolved in water for injection, a process that occurs spontaneously. Prior to creation of the suspension with antigen, the lipids can be easily sterilized by filtration or other means. However, the requirement for centrifugation of the large vesicles in the final aqueous suspension requires the maintenance of rigid sterile conditions, which may make the process awkward and difficult to use in a commercial process. Although different schemes may be used to create small unilamellar vesicles that could be sterile filtered, this would reduce the effect payload of the encapsulated antigen because the volume of a sphere, such as a liposome, decreases with the cube of the diameter. Furthermore, the materials cost for the antigen encapsulation would increase because the surface area only decreases with the square of the diameter, thus requiring more lipid for a given volume of encapsulated antigen.

In view of these manufacturing difficulties, the challenge exists to be able to create liposome vaccine formulations that can be created in a closed sterile environment, such as an injection vial, and that can be loaded externally with antigen for self-assembly of the liposomal antigen formulations. Therefore in one embodiment, the present invention solves many of the above-described problems with liposome vaccine formulations by providing liposomes including binding sites for T4 bacteriophages that display one or more antigens on the surface of the bacteriophage.

Figure 2:
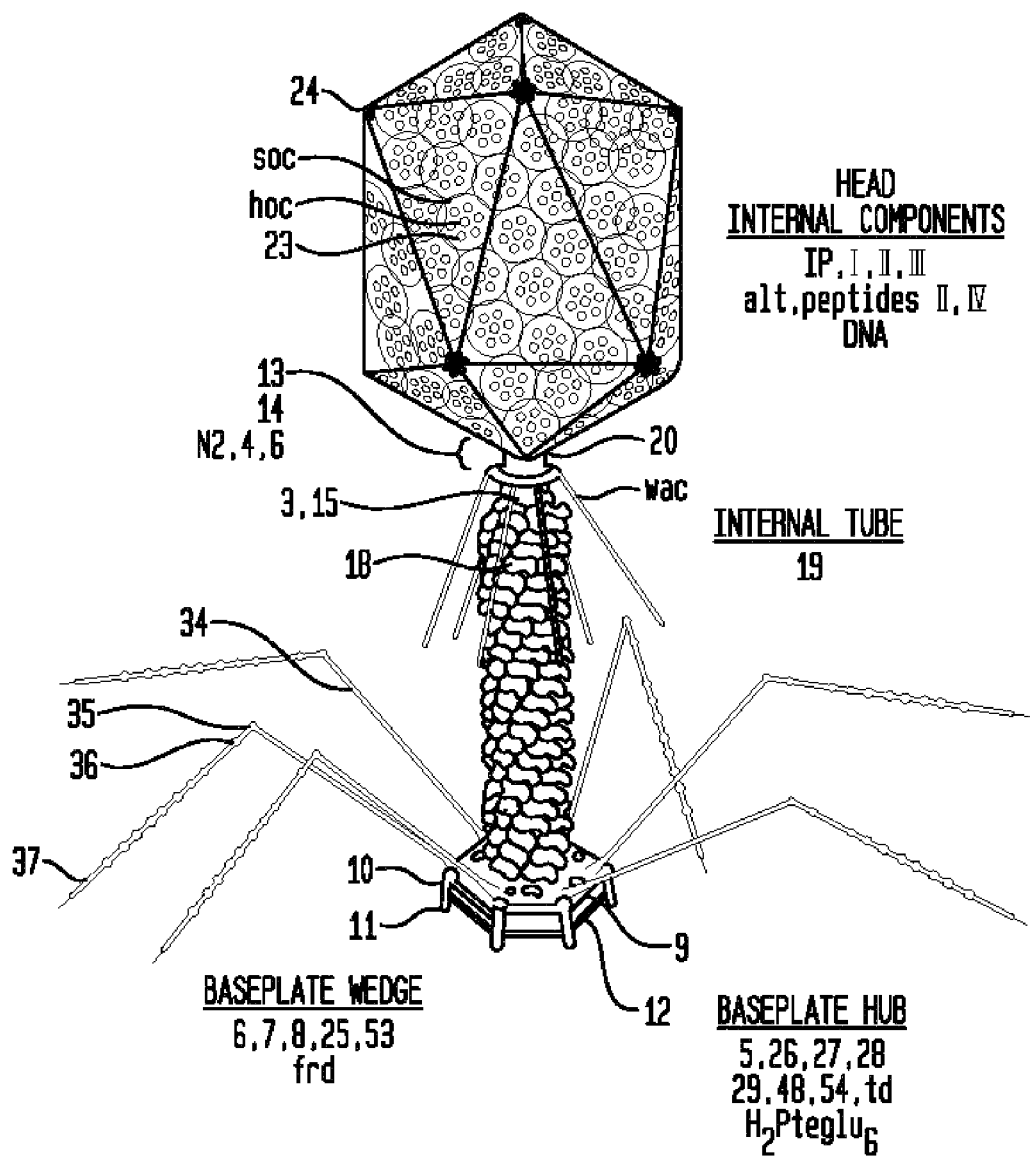
FIG. 2 is a schematic drawing of a T4 bacteriophage.

The T4 Bacteriophage (or bacteriophage T4), see FIG. 2, is a non-enveloped lytic virus that infects the bacterium, *Escherichia coli*. The infection process of phage T4 begins with the adsorption of specific receptors on the bacterial cell wall. Binding occurs through the tail fibers. Although some *E. coli* strain-specificity exits for T4 bacteriophage binding, one common feature for all binding is a dependence on lipopolysaccharide (LPS). LPS is a complex molecule consisting of a lipid core and branched sugars. It has previously been reported that certain glucosyl-conjugated, or glycosyl analog-conjugated, molecules on lipopolysaccharides can serve as partial receptors or as sites for phage binding to Gram negative bacteria described Dawes, J., *Nature,* 256:127-128 (1975) and Prehm, P., Jann, B., Jann, K., Schmidt, G., Strim, S., B. *J. Mol. Biol.,* 101:277-281 (1976), the entire contents and disclosures of which are hereby incorporated by reference. Studies have also shown that glucose residues of LPS can partially substitute for OmpC, another T4 bacteriophage binding molecule as described in Yu, F., Mizushima, S., *J. Bacteriol.,* 151 (2):718-722 (1982), the entire contents and disclosure of which is hereby incorporated by reference. The glucose moiety of LPS is one of the functional groups involved in the initial attachment of phage T4 tail fibers to *E. coli*. T4 binds to liposomes containing Glucer but not to liposomes lacking Glucer or containing Galcer. Glucer dependent attachment of T4 to liposomes appears to facilitate capsid-liposome interactions further stabilizing the complexes.

Figure 3:
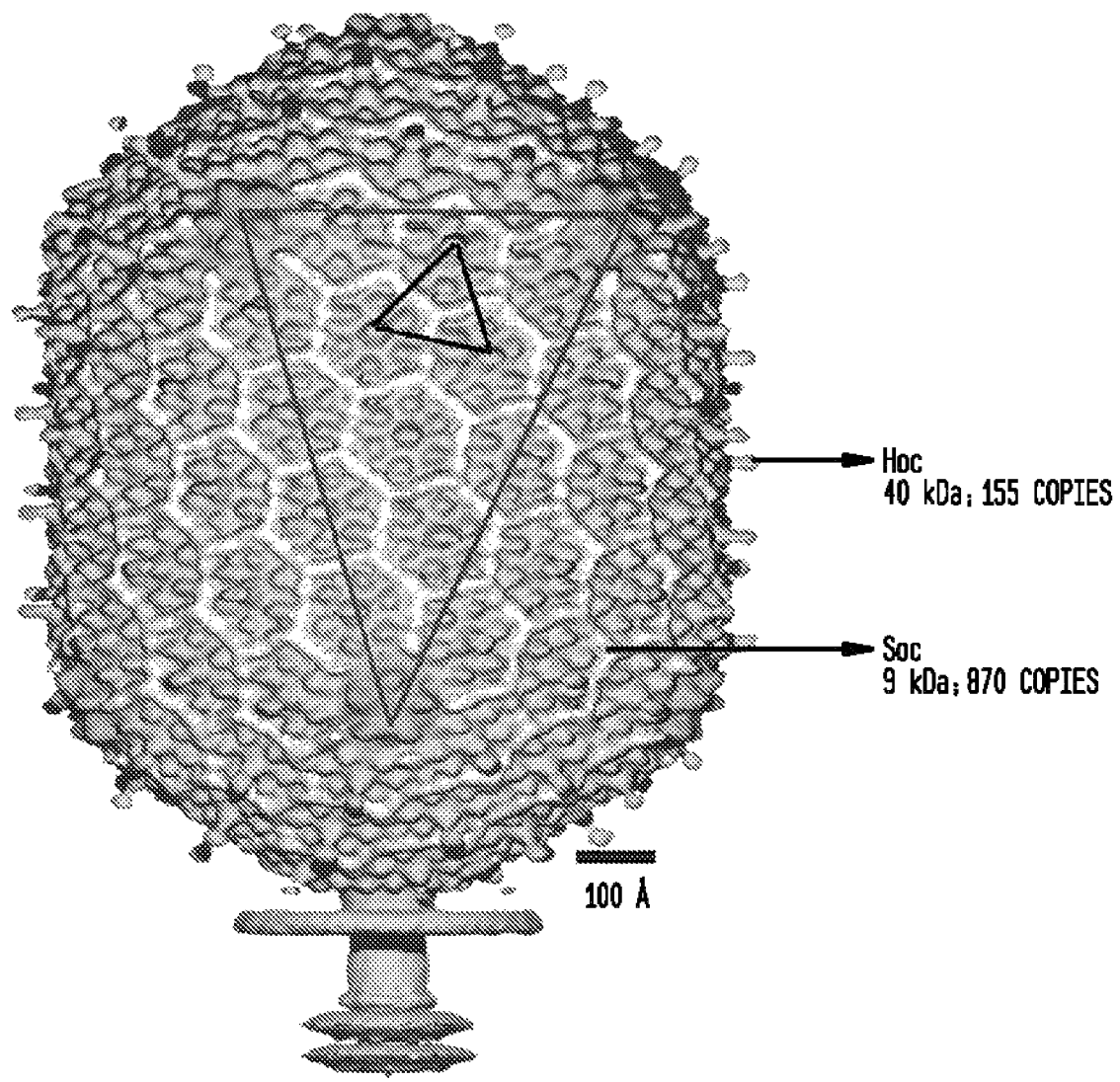
FIG. 3 is cryo EM reconstruction at 22 Å of the capisid of the T4 bacteriophage.

The capsid of the T4 bacteriophage is a prolate (elongated) icosahedron, as can be seen in FIG. 2 and as described in Leiman P G, Kanamaru S, Mesyanzhinov V V, Arisaka F. Rossmann M G., *Cell. Mol. Life. Sci.*, 60 (11):2356-2370 (2003), the entire contents and disclosure of which is hereby incorporated by reference. T4 contains 960 copies of a single major capsid protein, gp23. In addition, as shown in FIG. 3, there are two non-essential capsid proteins, the highly antigenic outer capsid protein (Hoc) and the small outer capsid protein (Soc). There are 155 copies of Hoc and 870 copies of Soc per capsid. These proteins are added onto the capsid after completion of capsid assembly and are not required for phage viability or phage infectivity. Because of this property, they can be replaced by foreign antigens, thus making T4 an exquisitely versatile nanoparticle. Immunogenicity data has been previously provided with T4 bacteriophage loaded with antigens from *Bacillus anthracis* and HIV, and it has been shown that T4 can effectively display one or more antigens in Li, Q., Shivachandra, S. B., Zhang, Z. and Rao, V. B., "Assembly of the Small Outer Capsid protein, Soc, on bacteriophage T4: a novel system for high density display of multiple large anthrax toxins and foreign proteins on phage capsid" in *J. Mol. Biol.*, 370:1006-1019 (2007) and Li, Q., Shivachandra, S., Leppla, S. H. and Rao, V. B., "Bacteriophage T4 Capsid: Unique Platform for Efficient Surface Assembly of Macromolecular Complexes" in *J. Mol. Biol.*, 363: 577-578 (2006), and Shivachandra, S., Rao, M., Janosi, L., Sathaliyawala, T., Matyas, G. R., Alving, C. R., Leppla, S. H., Rao, V. B., "In vitro binding of anthrax protective antigen on bacteriophage T4 capsid surface through Hoc-capsid interactions: a strategy for efficient display of large full-length proteins" in *Virology*, February 5; 345 (1):190-8. Epub 2005 Nov. 28 (2006), Sathaliyawala, T., Rao, M., Maclean, D. M., Birx, D. L., Alving, C. R. and Rao, V. B. Assembly of Human Immunodeficiency Virus (HIV) antigens on Bacteriophage T4: a Novel In vitro Approach To Construct Multicomponent HIV Vaccines. *J. Virol.* 80: 7688-7698 (2006), the entire contents and disclosures of which are hereby incorporated by reference.

This T4-protective antigen/HIV antigen complex is highly immunogenic in animals in Shivachandra, S. B., M. Rao, L. Janosi, T. Sathaliyawala, G. R. Matyas, C. R. Alving, S. H. Leppla, and V. B. Rao., *Virology*, 345 (1):190-8 (2006) and in Shivachandra S B, Li Q, Peachman K K, Matyas G R, Leppla S H, Alving C R, Rao M, Rao V B., *Vaccine,* 25 (7):1225-35. Epub 2006 Oct. 17 (2007), Sathaliyawala, T., Rao, M., Maclean, D. M., Birx, D. L., Alving, C. R. and Rao, V. B. Assembly of Human Immunodeficiency Virus (HIV) antigens on Bacteriophage T4: a Novel In vitro Approach To Construct Multicomponent HIV Vaccines. *J. Virol.* 80: 7688-7698 (2006), the entire contents and disclosures of which are hereby incorporated by reference. In addition to in vitro displaying HIV antigens, DNA expressing sequences for HIV proteins can also be packaged into the capsid of T4 in the absence of T4 bacteriophage DNA thus providing another avenue for increasing immunogenicity. A 30 Kb segment of foreign DNA has been successfully packaged into the capsid of T4. Liposomal vesicles have been safely administered to humans in several Phase I clinical trials as described in Fries L F, Gordon D M, Richards R L, Egan J E, Hollingdale M R, Gross M, Silverman C, Alving C R, *Proc. Natl. Acad. Sci.* (USA), 89:358-362 (1992) and Gluck, R., *Vaccine,* 17:1782-1787 (1999), the entire contents and disclosure of which is hereby incorporated by reference.

It has been found that T4 bacteriophage will bind to an exposed glucose unit of a glucoconjugate. This allows a T4 bacteriophage to be bound to many different types of substrates. The substrate may be any shape or size. For example, the substrate may be a sheet of material, a block of material, a layer or bi-layer of material, a film, a particle, etc.

The substrate of the present invention may be made from any type of material to which a glucoconjugate may be bound. For example, the substrate of the present invention may be any type of biological material, either natural or synthetic such as a liposome, lipid bilayer, a carbohydrate, protein, micelle, and polymer, etc. A polymer is a substance composed of molecules with large molecular mass composed of repeating structural units, or monomers, connected by covalent chemical bonds. While the term "polymer" in popular usage suggests "plastic", polymers comprise a large class of natural and synthetic materials with a variety of properties and purposes. Natural polymer materials such as shellac and amber have been in use for centuries. Biopolymers such as proteins (for example hair, skin and part of the bone structure) and nucleic acids play crucial roles in biological processes. A variety of other natural polymers exist, such as cellulose, which is the main constituent of wood and paper. Another example is polypropylene [poly(1-methylethylene)].

In addition to glucosyl ceramide (GC), there are various glucoconjugates that may be used in various embodiments of the present invention. A glucoconjugate is a type of glycoconjugate that consists of glucose, and molecules with an underlying glucose structure, such as glucosamine, that is linked to other types of molecules. Glucoproteins, proteoglycans and glucose-linked glycolipids (including glucosyl ceramide), and glucan molecules are the most abundant glucoconjugates found in mammalian cells and in mammalian tissues and noncellular spaces in mammals. They are found predominantly on the outer cell wall and in secreted fluids. Glycoconjugates and glucoconjugates have been shown to be important in cell-cell interactions due to the presence on the cell surface of various glucan and glycan-binding receptors in addition to the glycoconjugates and glucoconjugates themselves.

The term glycan refers to a polysaccharide, or oligosaccharide. Glycan may also be used to refer to the carbohydrate portion of a glycoconjugate, such as a glycoprotein, glycolipid, or a proteoglycan. Glycans usually consist solely of O-glycosidic linkages of monosaccharides (including glucose). For example, cellulose is a glycan (or more specifically a glucan) composed of beta-1,4-linked D-glucose, and chitin is a glycan composed of beta-1,4-linked N-acetyl-D-glucosamine. Glycans can be homo or heteropolymers of monosaccharide residues, and can be linear or branched.

A glucan molecule is a polysaccharide of D-glucose monomers linked by glycosidic bonds. The following are examples of glucans that may be suitable as binders for various embodiments of the present invention: cellulose, β-1,4-glucan, Curdlan, β-1,3-glucan, zymosan, β-1,3-glucan, dextran, a-1,6-glucan, glycogen, a-1,4- and a-1,6-glucan, laminarin, β-1,3- and β-1,6-glucan, lentinan, a strictly purified beta-1,6:beta-1,3-glucan, lichenin, pullulan, a-1,4- and a-1,6-glucan, starch, a-1,4- and a-1,6-glucan, Additional examples of glucoconjugates that may be used in various embodiments of the present invention would include synthetic conjugates in which a monosaccharide, oligosaccharide, or polysaccharide containing glucose as a constituent (and molecules with an underlying glucose structure, such as glucosamine) are chemically covalently or non-covalently attached to a particulate or polymer structure.

When the substrate is a liposome and the glucoconjugate used as a binder is glucosyl ceramide, glucosyl ceramide may be inserted into the liposomal lipid bilayer. The glucosyl ceramide then serves as a binding site for bacteriophage T4 for accumulating antigen on the surface of the liposomes. The glucosyl ceramide would be expected to have free lateral mobility in the lipid bilayer and could therefore be self-associate for multivalent binding of the glucose-binding sites on the tails of the bacteriophages, and this would result in high affinity binding that would be greater than the low affinity binding that would be expected from monovalent binding to soluble glucose moieties. Since the bacteriophages are much smaller than the liposomes, the surface of the liposomes may be covered with bacteriophages displaying one or more antigens.

The T4-liposome-GC conjugate that is formed by the above method may serve as a carrier of antigen by displaying the antigen on the surface of the T4 capsid (for example, as Hoc- or Soc-fusion proteins), or by expression of DNA for a given antigen inserted into the T4 capsid.

Since the binding involve self-assembly of the bacteriophage particles on the surface of the liposomes in the aqueous medium, this would eliminate the necessity to add the antigen to the liposomes during the manufacturing process. As an example, the bacteriophage particles and the lipids may spontaneously form liposomes and could be mixed together as sterile powders in an injection vial, and the liposomes containing the bound bacteriophage particles displaying antigen could then be formed simply by adding water to the injection vial.

In one embodiment the present invention may provide a self-assembling nanovaccine that combines a high degree of specificity with a high capability of immuno-stimulation, including the induction of unique neutralizing antibodies.

When T4 bacteriophages target bacteria, the challenge is to mimic nature by developing a natural target on a biodegradable particle. Liposomes have proven to have robust immuno-stimulating capacity but have drawbacks in manufacturing and stability: the challenge is to make liposome formulations that could be easily manufactured and that would be inexpensive but would retain enormous immuno-stimulating characteristics.

A number of high impact adjuvants for vaccines may be used. One key aspect of vaccine development is the need for appropriate adjuvanting. Nanovaccine adjuvants are presented and created here through the activation of numerous immunological activities including neutralizing antibodies.

All of the properties described herein concerning liposomes lead to the ability of liposomes to induce strong immunological responses. Self-assembling formulations of liposomes, named WRAIR liposomes, were invented in our laboratory at the Walter Reed Army Institute of Research. WRAIR liposomes are composed of dimyristoyl phosphatidyl-choline (DMPC), dimyristoyl phosphatidylglycerol (DMPG), cholesterol, and lipid A (Alving, C. R., Shichijo, S., Mattsby-Baltzer, I., Richards, R. L., Wassef, N. M. 1993. Preparations and use of liposomes in immunological studies. In *Lipsosome Technology*: G. Gregoriadis, ed., CRC Press Inc., Boca Raton, Fla., Vol. 3, p. 317-343; Wassef, N. M., Alving, C. R., Richards, R. L. 1994. Liposomes as carriers for vaccines. Immuno Methods. 4, 217-222). They have greater manufacturing reproducibility than traditional liposomes and can be made under GMP conditions. WRAIR liposomes also have extended shelf-life compared to traditional liposomes, which makes them attractive for therapeutic and vaccine products. Preliminary data using surface plasmon resonance indicated that phage T4 bound 6-fold better to WRAIR liposome containing glucocerebroside than to WRAIR liposomes lacking glucocerebroside, lipid A or containing galactose cerebroside, see FIGS. 4 and 8.

HIV is an enveloped virus which derives its membrane from host cells. The structure and orientation of viral proteins is likely influenced by the lipid bilayer in which they are imbedded. Liposome formulations can emulate the surface of the virus envelope and may be advantageous in the proper presentation of the HIV envelope proteins. In addition to the antigens presented on T4, we will also incorporate HIV envelope proteins into the liposome formulations.

A self-assembling nanoparticle that displays antigen (HIV protein and/or DNA) with a high degree of specificity and a high capability of immuno-stimulation including inducing HIV neutralizing antibodies can be created by utilizing the property of T4 receptors to bind to engineered liposomes containing glycolipids and the adjuvant lipid A.

The overall objective is to create a self-assembling nanovaccine that combines a high degree of specificity with a high capability of immuno-stimulation specifically in the induction of neutralizing antibodies.

In one embodiment of the present invention, there is provided T4 bacteriophages containing antigen attached to or contained within the T4 capsid. Virtually any antigen may be used in conjunction with the T4 bacteriophages, and in some of these embodiments, the antigen is an HIV envelope antigen. In alternative embodiments, the T4 bacteriophage may be altered so as to comprise DNA sequences encoding one or more HIV antigens, particularly HIV proteins. In these embodiments, the HIV antigen encoding sequences will be packaged into the capsid of T4, either in the presence or in the absence of T4 bacteriophage DNA, thus providing another avenue for increasing immunogenicity. Packaging of foreign DNA may be accomplished either in the infected *Escherichia coli* cell during the course of infection, or in the test tube using a defined packaging system consisting of purified components such as empty capsids, packaging proteins, foreign DNA, and ATP as described in Jiang, J., Abu-Shilbayeh, L. and Rao, V. B. "Display of a PorA Peptide form *Neisseria meningitidis* on the Bacteriophage T4 Capsid surface" in *Infection and Immunity* 65:4770-4777 (1997), Ren, Z. J., Lewis, G. K., Wingfield, P. T., Locke, E. G., Steven, A. C., Black, L. W., "Phage display of intact domains at high copy number: a system based on SOC, the small outer capsid protein of bacteriophage T4" in *Protein Science* 5:1833-43 (1996), Kondabagil, K. R., Zhang, Z. B. and Rao, V. B. The DNA translocating ATPase Of bacteriophage T4 packaging motor. *J. Mol. Biol.,* 363: 786-799 (2006) and in Black, L. W. and Peng, G. "Mechanistic coupling of bacteriophage T4 DNA packaging to components of the replication-dependent late transcription machinery" in *J. Biol. Chem.,* 281:25635-43 (2006), the entire contents and disclosures of which are hereby incorporated by reference.

In one embodiment of the present invention, there is provided a method of manufacturing multilamellar liposomes. These liposomes in some embodiments may be used directly for immunization, or can be incorporated into an oil-in-water emulsion. The present formulations and manufacturing methods provide several advantages, among which include the advantage of providing liposomes containing bonding sites for bacteriophage T4 that displays antigen on the surface of the bacteriophage T4 capsids.

According to yet another aspect of the present invention, the liposomes as described herein can also be used to characterize T4 bacteriophage receptor binding to glycolipids embedded in a lipid bilayer.

The liposomes and liposomal formulations are highly versatile and can be prepared either as nanoparticles or as mixtures of varying sizes. In addition, the liposomes of the present invention, in some embodiments, can be engineered with different phospholipid compositions, as well as different ratios of these phospholipids. Antigens can be reconstituted within the lipid bilayers of the liposomes; encapsulated within the internal aqueous spaces; or covalently attached to the outer surface.

Suitable adjuvants for use in embodiments of the present invention include: lipid A, as well a gel-type adjuvants including: aluminum salts or "alum adjuvants" such as aluminum hydroxide and aluminum phosphate, calcium salts such as calcium phosphate, etc.; microbial adjuvants including muramyl dipeptide (MDP) derivatives such as murabutide and threonyl-MDP, bacterial endotoxins such as monophosphoryl lipid A, bacterial DNA such as CpG and bacterial exotoxins such as cholera tox (CT), *Escherichia coli* heat-labile enterotoxn (LT), etc.; particulate adjuvants including biodegradable polymer microspheres, immunostimulatory complexes (ISCOMs), liposomes such as virosomes, etc.; oil emulsions and surfactants including Freund's incomplete adjuvant, montanide ISA 720, etc., microfluidized emulsions including MF59, AS02A, etc., saponins including QS-21, etc.; synthetic adjuvants including nonionic block copolymers, polyphosphazene (PCPP), synthetic polynucleotides such as Poly A:U, Poly A:C, etc.; cytokines such as interleukin (IL)-2, IL-12, granulocyte-macrophage colony-stimulating factor (GM-CSF); interferon gamma (IFN-γ), etc., genetic adjuvants including cytokine gene or genes encoding costimulatory molecules delivered as plasmid DNA such as IL-12, IL-2, IFN-γ, etc. and other adjuvants described by Alving, C. R. Vaccine adjuvants. in *Vaccines for Biodefense and Emerging and Neglected Diseases*, Barrett, A., and Stanberry, L., eds., Elsevier, N.Y. (2008) (in press).

Figure 5:
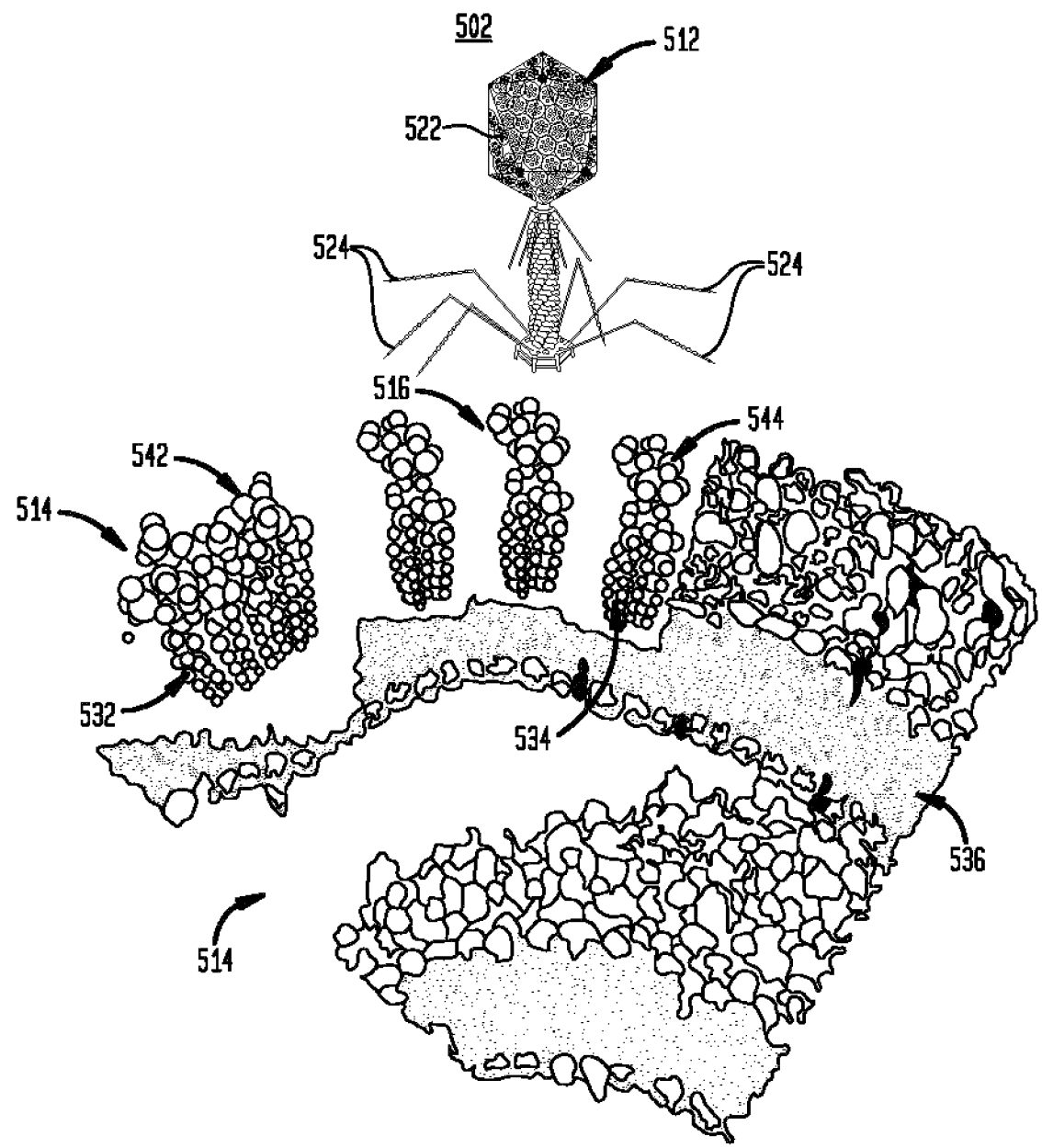
FIG. 5, is a schematic illustration showing part of a T4 bacteriophage-glucosyl ceramide-lipid A-liposome as an adjuvanted protein or DNA vaccine in accordance with one embodiment of the present invention.

An illustrative embodiment is presented at FIG. 5 of T4 bacteriophage-glucosyl ceramide-lipid A-liposome complex 502 as an adjuvanted protein according to one embodiment of the present invention. Complex 502 includes a T4-bacteriophage 512, lipid A molecules 514, glucosyl ceramide molecules 516 and a liposome 518. Bacteriophage 512 includes a capsid 522 and tails 524. As can be seen in FIG. 5, hydrocarbon tails 532 of each lipid A molecule 514 and hydrocarbon tail 534 of each glucosyl ceramide molecules 516 are embedded in lipid bilayer 536 of liposome 518. Each lipid A molecule 514 also includes two glucosamine units 542 and each glucosyl ceramide molecule 516 includes a glucose unit 544. Tails 524 of bacteriophage 512 are in the process of binding with glucosyl ceramide molecules 516.

For clarity of illustration in FIG. 5, only part of the liposome is shown and only one T4 bacteriophage of the many bacteriophages bound to the liposome are shown. Also, for clarity of illustration, the component parts of the complex are not shown to scale. Depending on the embodiment of the invention, the bacteriophage may have antigens on the surface of the capsid or the bacteriophage DNA encapsulated in the capsid may be replaced with another type of DNA.

When used as a vaccine, such a complex may be ingested by a phagocytic cell that serves as an antigen presenting cell (APC). The APC may be activated by the lipid A in the complex provides an adjuvant effect. The expression of the capsid antigen provides an expression of an antigen. The expression of the antigen, enhanced by the adjuvant effect provides an immune response.

In an alternative embodiment, the complex of FIG. 5 may be used as a DNA vaccine. When used as a DNA vaccine, the DNA in the T4 is released after the complex is ingested by the phagocytic cell.

In one embodiment of the present invention, phage T4 may also be covalently coupled to liposomes by incorporating very small amounts of a sulfhydryl reactive lipid, cholest-5-en-3B (dithiopyridine) (PDS-cholesterol) to covalently couple to free SH groups available anywhere on phage T4 surface. Similar reagents such as the primary amino group specific 1,2 Dipalmitoyl-sn-Glycero-3-phosphoehtnaola-mine-N-[4-(p-maleimidophenyl)butyramide (MPB) commercially available from Avanti polar Lipids can also be used and such reagents, Kung, V. T., and Redemann, C. T., "Synthesis of carboxyacyl derivatives of phosphotidylethanola-mine and use as an efficient method for conjugation of protein to liposomes" in *Biochim. Biophys. Acta.* 862:435-439 (1986), the entire contents and disclosure of which is hereby incorporated by reference.

Ligand-receptor binder systems may also be used as a T4-liposome binder. For example, T4-capsid-exposed hydrophobic ends of proteins or peptides displayed on T4 are ideally suited to form efficient interactions with liposomes alone or liposomes containing an appropriate receptor. One example is the MPER (membrane proximal external region) of HIV gp41 envelope protein can interact with the liposomes alone through nonspecific hydrophobic interactions or can form specific ligand-receptor binder interactions with gp120 receptor incorporated into a liposome. Biochemical studies have previously demonstrated that MPER peptides interact with liposomes or phospholipid micelles through the C-terminal hydrophobic sequences described in Sanchez-Martinez, S et al., "Specific phospholipid recognition by human immunodeficiency virus type-1 neutralizing anti-gp41 antibody" in *FEBS Letters*, 580:2395-2399 (2006) and Shnaper, S et al., "The C- and N-terminal regions of gp41 ectodomain fuse membranes enriched and not enriched with cholesterol, respectively" in *J. Biol. Chem.* 279:18526-18534 (2004), the entire contents and disclosures of which are hereby incorporated by reference. Therefore there can be efficient spontaneous interaction of the T4-Soc or Hoc-MPER particles with synthetic liposomes through tail fibers and capsids.

Other examples of ligand-receptor systems include: T4-Hoc fusion proteins or T4-Soc fusion proteins including gp120 as the ligand and CD4 as the receptor, T4-Hoc fusion proteins or T4-Soc fusion proteins including anthrax protective antigen as the ligand and anthrax toxin receptor (ATR) as the receptor, etc.

U.S. Patent Application No. 2005/0226892 to Rao, entitled "Methods and compositions comprising bacteriophage nanoparticles," filed Oct. 3, 2005 describes ways of making customized T4 bacteriophages that may be used in the method and composition of the present invention and the entire contents and disclosure of this patent application is hereby incorporated by reference. In the customized T4 bacteriophages of Rao, Hoc and/or Soc fusion proteins are bound to the capsid of the T4 bacteriophage and the copy number and/or ratio of one or more Hoc fusion protein on each capsid is controlled and/or the copy number and/or ratio of the one or more Soc fusion proteins on each capsid is controlled. As described in U.S. Patent Application No. 2005/0226892 to Rao, some customized bacteriophages may have just one or more types of Hoc fusion proteins, some customized bacteriophages may have just one or more types of Soc fusion proteins, and some customized bacteriophages may have mixtures of Hoc and Soc fusion proteins. Although for simplicity the term "T4 bacteriophage" is used below, it should be understood that the embodiments described below may use T4 bacteriophage derivatives, such as T4 empty capsids and capsids with DNA as well.

In one embodiment, a customized T4 bacteriophage of the present invention may be formed in an in vitro assembly system that utilizes a hoc⁻ and/or soc⁻ T4 bacteriophage and a Hoc and/or Soc protein or a fragment thereof fused to another molecule. This molecule may comprise any molecule having chemical and/or biological activity, including but not limited to a protein, protein fragment, amino acid, antigen, lipid, antibody, carbohydrate, enzyme, cytokine or chemokine or other inflammatory mediator. It may be possible to fuse the molecule to Hoc and/or Soc by any method known to those of skill in the art. When this molecule is fused to a Hoc and/or Soc protein or a fragment thereof, the resulting product comprises a Hoc and/or Soc fusion-molecule. In one embodiment of the present invention, the molecule fused to Hoc and/or Soc is a protein such as a foreign protein, thus creating a Hoc and/or Soc fusion protein. A Hoc and/or Soc fusion protein may be formed comprising a foreign antigen and the Hoc and/or Soc protein. After purification, these Hoc and/or Soc fusion proteins are combined with purified hock and/or soc⁻ T4 bacteriophage particles. The resultant customized T4 bacteriophage displays, for example, foreign antigen fused to the Hoc.

To create the Hoc and/or Soc fusion protein according to one embodiment of the present invention, one fuses the N- or C-terminus of a Hoc and/or Soc protein or fragment thereof to a foreign molecule or entity such as a protein. In certain embodiments of the present invention, a hexahistidine tag sequence is added to the N-terminus of the fusion protein to allow for a single-step purification of the protein-Hoc and/or Soc recombinant protein by Ni-agarose column chromatography. One skilled in the art would recognize that instead of a hexahistidine-tag, one may use numerous other tags known in the art for the purification of the recombinant proteins, including but not limited to glutathione transferase (GST), maltose binding protein (MBP), FLAG, hemaglutinin (HA), and green fluorescent protein (GFP). The invention further comprises a generic linker sequence between the foreign protein and the Hoc or Soc protein. In certain embodiments, the linker is a structureless linker. Though not wishing to be bound by the following theory, it is thought that the linker sequence minimizes interference by the foreign protein domain on Hoc or Soc folding or assembly to the capsid surface and vice versa. In certain embodiments, the structureless linker preferably comprises a polyglycine linker (pro-gly-gly), but a variety of linkers, structured and structureless and varying in length and in sequence that are known in the art are compatible with the one or more embodiments of the present invention.

The Hoc and/or Soc fusion protein embodiment of the present invention may be constructed using a variety of methods. One skilled in the art will appreciate that multiple genetic and protein engineering methods are available for the construction of the Hoc and/or Soc fusion protein. For example, one may use a PCR-directed Splicing by Overlap Extension (SOE) strategy to engineer the gene constructs encoding the desired fusion protein described in Horton, R. M., Hunt, H. D., Ho, S, N., Pullen, J. K.& Pease, L. R., "Engineering hybrid genes without the use of restriction enzymes: gene splicing by overlap extension" in *Gene*, 77, 61-68 (1989) and in Kuebler, D. and Rao, V. B., "Functional Analysis of the DNA Packaging/Terminase Protein Gp17 from Bacteriophage T4" in *J. Mol. Biol.*, 281:803-814 (1998), the entire contents and disclosure of which are hereby incorporated by reference. This strategy requires four oligonucleotides (Primers 1-4) and three successive PCRs and is a rapid and powerful strategy for engineering recombinant constructions. Using this strategy, fairly complex gene constructions can be engineered and multiple gene fusions completed in a single day. To include the hexahistidine tag sequence according to certain embodiments of the present invention, one may insert the gene construct in-frame to a hexa-histidine tag of the T7 expression vector.

The vector can be a typical *E. coli* expression vector such as pET vector described in Studier, W., Rosenberg, A. H. & Dunn, J. J., "Use of T7 RNA polymerase to direct expression of cloned genes" in *Methods Enzymol.*, 185, 61-89 (1990), the entire contents and disclosure of which is hereby incorporated by reference, or one among a vast array of insect, mammalian, and shuttle expression vectors that are commercially available. The over-expressed antigens will be purified either from soluble cell-free lysate, or insoluble inclusion bodies by denaturation and renaturation. Purification strategies include column chromatographies such as Histrap affinity, MonoQ ion-exchange, and Superdex gel filtration, etc. such as described in Shivachandra S. B., Rao M., Janosi L., Sathaliyawala T., Matyas G. R., Alving C. R., Leppla S. H., Rao V. B., "In vitro binding of anthrax protective antigen on bacteriophage T4 capsid surface through Hoc-capsid interactions: a strategy for efficient display of large full-length proteins" in *Virology*, 345: 190-198 (2006), the entire contents and disclosure of which is hereby incorporated by reference.

In one embodiment of the present invention, comprises a T4 bacteriophage particle of comprising a defined prolate i.e. elongated icosahedron with a diameter of about 86 nm and a length of about 120 nm. To permit Hoc and/or Soc binding to the capsid of the T4 bacteriophage particle, the present invention utilizes a hoc⁻ and/or soc⁻ T4 bacteriophage mutant that is incapable of expressing Hoc and/or Soc protein; thus, this mutant does not contain Hoc and/or Soc proteins on its capsid surface as described in Shivachandra S. B., Rao M., Janosi L., Sathaliyawala T., Matyas G. R., Alving C. R., Leppla S. H., Rao V. B., "In vitro binding of anthrax protective antigen on bacteriophage T4 capsid surface through Hoc-capsid interactions: a strategy for efficient display of large full-length proteins" in *Virology*, 345: 190-198 (2006), the entire contents and disclosure of which is hereby incorporated by reference. The method of creating a hoc⁻ and/or soc⁻ T4 bacteriophage mutant may be carried out by various methods known in the art, see appendices in Karam, J. D. (ed.), Molecular Biology of Bacteriophage T4. 1994 ASM Press, Washington, D.C., the entire contents and disclosure of which is hereby incorporated by reference. For use in the in vitro system of the present invention, the hoc⁻ and/or soc⁻ T4 bacteriophage particles need to be isolated and should be substantially pure. One may isolate these T4 bacteriophage particles by any means known in the art, but adequate isolation and purification may be achieved for example through sucrose gradient purification as described in Mooney, D. T., et al. *J. Virol.* 61, 2828-2834 (1987), the entire contents and disclosure of which are hereby incorporated by reference.

Following the purification the Hoc and/or Soc fusion proteins according to certain embodiments of the present invention and the isolation of hoc⁻ and/or soc⁻ T4 bacteriophage, the purified Hoc and/or Soc fusion protein is assembled or "loaded" onto the purified hoc⁻ and/or soc⁻ T4 bacteriophages by the in vitro assembly system to create T4 bacteriophages. Loading involves the placement of Hoc and/or Soc fusion proteins in close proximity to hoc⁻ and/or soc⁻ T4 bacteriophages so that the Hoc and/or Soc proteins bind to the T4 bacteriophage capsid surface. To facilitate loading of the Hoc and/or Soc fusion proteins onto the hoc⁻ and/or soc⁻ T4 bacteriophages, the purified components are incubated in a reaction buffer for about 1-120 min, preferably for about 20-90 min, more preferably for about 40-70 min, and even more preferably for about 30-60 min. During this incubation period, the reaction buffer temperature may vary, but is preferably around 25-45° C., and more preferably around 32-42° C., and even more preferably around 37° C. As for the reaction buffer, a variety of buffers known in the art are compatible with the present invention. For example, a suitable reaction buffer may comprise a Tris buffered saline at a pH between 7-8, or preferably at a pH between 7.2-7.8, and more preferably at a pH between 7.3-7.5, and even more preferably at a pH around 7.4. Other suitable reaction buffers may include those known those skilled in the art, for example, phosphate buffered saline, hepes buffer, and the like, at a variety of salt concentrations, and/or in the presence of many buffer components such as glycerol, sucrose, ionic and nonionic detergents.

After incubation of the Hoc and/or Soc fusion proteins with the hoc⁻ and/or soc⁻ T4 bacteriophages in the reaction buffer, the Hoc and/or Soc fusion protein-hoc⁻ and/or soc⁻ T4 bacteriophages are removed from the reaction buffer by methods known to those skilled in the art. For example, the reaction mixture (which includes the purified Hoc and/or Soc fusion proteins, the purified hoc⁻ and/or soc⁻ T4 bacteriophages, the reaction buffer, and the newly formed T4 bacteriophages) may be centrifuged at 5,000-40,000 rpm for 20-100 min, preferably at around 10,000-20,000 rpm for 40-80 min, and more preferably at around 13,000-16,000 rpm for 55-65 min. The particles can also be recovered through column chromatography or gradient centrifugation techniques. Following the centrifugation or recovery step, the supernatant containing unbound Hoc and/or Soc fusion protein is discarded and the pellet, which contains the newly formed T4 bacteriophages, is washed with reaction buffer or other suitable buffers to remove any unbound fusion protein.

In one embodiment, a customized T4 bacteriophage of the present invention has the advantage of having a defined copy number of Hoc and Soc binding sites (combined total of about 1025 copies per particle). With such a large number of defined binding sites, the T4 bacteriophages provide a unique nanoplatform upon which it may be possible to customize the display of a specific molecule or multiplicity of molecules. By manipulating the ratios of components in the in vitro assembly reaction (i.e., manipulating the ratio of Hoc and/or Soc fusion proteins to T4 bacteriophage particles) before or during the incubation period described above, the copy number of fusion proteins bound to the T4 bacteriophage can be controlled. Similarly, by using two or more Hoc and/or Soc fusion proteins in the in vitro assembly system and by adjusting the molar ratios of the different fusion proteins to the T4 bacteriophage, it may be possible to control the proportion of fusion proteins bound to the T4 bacteriophage to create a defined T4 bacteriophage. For example, a given T4 bacteriophage may display combinations of the HIV antigens, tat and nef, as well as other fusion proteins. By changing the ratios tat-Hoc and nef-Hoc fusion proteins to phage particles before or during the incubation period, the copy number of proteins displayed on phage will be proportionally altered. The fusion proteins bind to the binding sites independently and no interference or cooperativity between the binding of different proteins has been observed. The methods for controlling the copy number has been described in Li, Q., Shivachandra, S. B., Zhang, Z. and Rao, V. B. Assembly of the Small Outer Capsid protein, Soc, on bacteriophage T4: a novel system for high density display of multiple large anthrax toxins and foreign proteins on phage capsid. *J. Mol. Biol.*, 370:1006-1019 (2007), and Shivachandra, S. B., Li, Q., Peachman, K. K., Matyas, G. R., Leppla S. H., Alving C. R., Rao, M., Rao V. B. Multicomponent anthrax toxin display and delivery using bacteriophage T4. *Vaccine*, 25:1225-35 (2007).

Using the in vitro assembly system, it may be possible to construct a multitude of different customized T4 bacteriophages for use in a variety of applications. For example, certain embodiments of the present invention are capable of generating both humoral and cell-mediated immune responses and are thus useful as single or multicomponent vaccine formulations. In these various vaccine formulations, the foreign protein of the Hoc and/or Soc fusion protein may comprise an antigenic protein that is displayed on the surface of a T4 bacteriophage particle. Various antigens include, but are not limited to, Interleukin-1 ("IL-1"), Interleukin-2 ("IL-2"), Interleukin-3 ("IL-3"), Interleukin-4 ("IL-4"), Interleukin-5 ("IL-5"), Interleukin-6 ("IL-6"), Interleukin-7 ("IL-7"), Interleukin-8 ("IL-8"), Interleukin-10 ("IL-10"), Interleukin-11 ("IL-11"), Interleukin-12 ("IL-12"), Interleukin-13 ("IL-13"), lipid A, phospholipase A2, endotoxins, staphylococcal enterotoxin B and other toxins, Type I Interferon, Type II Interferon, Tumor Necrosis Factor (TNF-α. or b), Transforming Growth Factor-β. ("TGF-β"), Lymphotoxin, Migration Inhibition Factor, Granulocyte-Macrophage Colony-Stimulating Factor ("CSF"), Monocyte-Macrophage CSF, Granulocyte CSF, vascular epithelial growth factor ("VEGF"), Angiogenin, transforming growth factor ("TGF-β"), heat shock proteins, carbohydrate moieties of blood groups, Rh factors, fibroblast growth factor, and other inflammatory and immune regulatory proteins, nucleotides, DNA, RNA, mRNA, sense, antisense, cancer cell specific antigens; such as MART, MAGE, BAGE, and heat shock proteins (HSPs); mutant p53; tyrosinase; mucines, such as Muc-1, PSA, TSH, autoimmune antigens; immunotherapy drugs, such as AZT; and angiogenic and anti-angiogenic drugs, such as angiostatin, endostatin, and basic fibroblast growth factor, and vascular endothelial growth factor (VEGF), prostate specific antigen and thyroid stimulating hormone, or fragments thereof. And as described above, by adjusting the molar ratios of Hoc and/or Soc-antigen fusion proteins to hoc⁻ and/or soc⁻ T4 bacteriophage particles before or during the incubation period, one may tailor the T4 bacteriophage to display a single antigen, a multiplicity of antigens, and/or a defined proportion of antigens on the capsid of the T4 bacteriophage particle.

In certain embodiments of the present invention, it may be possible to use the in vitro assembly system to create customized T4 bacteriophages that simultaneously display multiple antigens corresponding to one or several infectious diseases. More specifically, by utilizing the in vitro assembly system described herein, it may be possible to display, for example, both HIV and anthrax antigens on the same capsid surface, allowing for the formulation of one vaccine against both HIV and anthrax. In another embodiment, the nanoparticle may be customized for diseases and disorders that manifest together or close in time. For example, many AIDS patients suffer from a variety of additional illnesses, such as tuberculosis. A customized nanoparticle could contain an antigen(s) (or various epitopes of an antigen(s)) of human immunodeficiency virus as well as mycobacteria. In an alternative embodiment, it may be possible to use the in vitro assembly system to create T4 bacteriophages that simultaneously display multiple epitopes of one, or more than one, antigen on the same capsid.

In another embodiment, site-directed combinatorial mutations can be introduced at the targeted sequence during the construction of Hoc and/or Soc gene fusion constructs as described in Rao, V. B. and Mitchell, M., "The N-terminal ATPase Site in the Large Terminase Protein Gp17 is Critically Required for DNA Packaging in Bacteriophage T4" in *J. Mol. Biol.*, 314: 411-421 (2001), the entire contents and disclosure of which is hereby incorporated by reference. Using this strategy, expression of a pool of antigen mutants and their combined display on the T4 bacteriophage or on multiple T4 bacteriophages will allow construction of a multi-variant vaccine that would be effective against several strains of an infectious agent, or an infectious agent that generates mutants against the selection pressure of the host (e.g., HIV).

In yet another embodiment, it may be possible to construct a customized T4 bacteriophage that displays interactive molecules on its surface. For instance, using methods known to those of skill in art, it may be possible to construct a first Hoc and/or Soc fusion protein that comprises Hoc and/or Soc fused to a first foreign protein. Similarly, it may be possible to construct a second Hoc and/or Soc fusion protein that comprises Hoc and/or Soc fused to a second foreign protein. By employing the in vitro assembly system disclosed herein, it may be possible to load both first and second Hoc and/or Soc fusion proteins onto the surface of a T4 bacteriophage. In certain embodiments, the first and second foreign proteins can individually present various immunological epitopes. Additionally, the first and second foreign proteins may interact with each other directly or indirectly through another protein or molecular component that can be added to the assembly reaction mixture. A T4 bacteriophage of this embodiment may, for example, impart additional immunogenicity to various T4 bacteriophage compositions of the present invention. Not wishing to be bound by the following theory, interactions between the first and second foreign proteins may, for example, expose additional epitopes and therefore enhance the immunogenic response. In a related embodiment, the first foreign protein may possess enzymatic activity while the second foreign protein may serve as a substrate or a ligand for the first foreign protein. In this embodiment, cleavage of the second protein may result in a variety of biological effects, including but not limited to the display of additional epitopes on the T4 bacteriophage surface. Also, the cleaved protein in such an embodiment may, for example, be a cytokine or chemokine that can further modulate the immune response. Although the above embodiments refer to first and second foreign proteins, the present invention also contemplates similar embodiments relying on a multiplicity of different foreign proteins. For example, a third foreign protein and a fourth foreign protein may also display additional epitopes individually and/or when interacting on the surface of the T4 bacteriophage particle. Protein engineering techniques known to those of skill in the art will allow manipulation of the structures of, and distances between, the displayed molecular components of these embodiments for a variety of specific applications. These are particularly important because the complexes envisioned either mimic, or are identical to, the native complex(es) formed in vivo through conformational transitions that occur following specific interactions. Such complexes likely generate specific immune responses that can interfere with the interactions between the infectious agent and the host cell (e.g., HIV infection of target host cells), the molecules of a multicomponent toxin to generate lethal toxicity (e.g., formation of anthrax lethal toxin and edema toxin).

In another embodiment of the present invention, a customized T4 bacteriophage of the present invention may include a second layer of molecules displayed over a first layer of displayed proteins. In this embodiment, the Hoc and/or Soc fusion proteins may comprise the first layer, and the foreign protein of the Hoc and/or Soc fusion protein serves as a nexus for the assembly of the second layer of molecular components. As such, the displayed first layer proteins can be used as binding sites to display second layer proteins that interact with these first layer binding sites. For instance, T4 bacteriophage-bound anthrax PA63 can be used to capture anthrax lethal toxin and edema toxin (not fused to Hoc or Soc), or a foreign protein that is fused to the N-terminal PA63 binding domain of LF or EF.

In yet another embodiment, it may be possible to design a customized T4 bacteriophage that target specific cell or tissue types. In particular, by displaying a Hoc and/or Soc-ligand fusion in which the ligand is specific for a cell and/or tissue type, it may be possible to target the T4 bacteriophage of the present invention to certain cells or tissues to elicit a variety of selective cellular or tissue responses. It may be possible to develop such a Hoc and/or Soc-ligand fusion molecule by any method known to those of skill in the art. Once developed, the Hoc and/or Soc-ligand fusion molecule can be loaded onto the hoc$^-$ and/or soc$^-$ T4 bacteriophage particles using the in vitro assembly system disclosed herein to create T4 bacteriophages displaying the ligand. Various ligands include, but are not limited to the ones that bind to CD4, chemokine receptors, GM-1 receptor, Toll-like/pathogen recognition receptors, DC-sign receptor, cytokine receptor, Fc receptor, or compliment receptors or fragments thereof.

In another embodiment of the present invention, it may be possible to use recombinant DNA technology and T4 genetics to package foreign DNA into a customized T4 bacteriophage's genome as described, for example, in Jiang, J., Abu-Shilbayeh, L. and Rao, V. B. "Display of a PorA Peptide form *Neisseria meningitidis* on the Bacteriophage T4 Capsid surface" in *Infection and Immunity* 65:4770-4777 (1997), Ren, Z. J., Lewis, G. K., Wingfield, P. T., Locke, E. G., Steven, A. C., Black, L. W., "Phage display of intact domains at high copy number: a system based on SOC, the small outer capsid protein of bacteriophage T4" in *Protein Science* 5:1833-43 (1996), Kondabagil, K. R., Zhang, Z. B., Rao, V. B., "The DNA translocating ATPase Of bacteriophage T4 packaging motor" in *J. Mol. Biol.*, 363: 786-799 (2006), Clark et al., *FEMS Immunology and Medical Microbiology*, 40, 21-26 (2004) and March et al., *Vaccine*, 22, 1666-1671 (2004), the entire contents and disclosures of which are hereby incorporated by reference. Thus, in addition to the display of Hoc and/or Soc fusion proteins on the surface of the T4 bacteriophage, a foreign DNA construct encoding an antigen or a Hoc and/or Soc fusion protein is present within the T4 bacteriophage. In certain embodiments, such a unique T4 bacteriophage platform technology can be used as a prime-boost delivery system. Generally, the immune responses obtained by plasmid DNA vaccination are poor and inconsistent; thus, multiple injections and large quantities of DNA and protein are required to enhance the immune responses. In contrast, the T4 bacteriophages of this embodiment can deliver both the protein and the DNA components simultaneously to the same antigen-presenting cell, thus potentially inducing more robust immune responses. For example, using phage genetics and molecular biology techniques known in the art, one could insert a DNA construct into the genome of a T4 bacteriophage under the control of a strong mammalian promoter such as the CMV (cyto megalo virus) promoter, which would express a fusion protein comprising, for example, the HIV antigen nef (i.e., the DNA construct would express a nef-Hoc fusion protein). Alternatively, by using specialized T4 packaging systems as described in Leffers, G. and Rao, V. B., "A discontinuous headful packaging model for packaging less than headful length DNA molecules by bacteriophage T4" in *J. Mol. Biol.*, 258:839-850 (1996), and Kondabagil, K. R., Zhang, Z. B. and Rao, V. B., "The DNA translocating ATPase Of bacteriophage T4 packaging motor" in *J. Mol. Biol.*, 363: 786-799 (2006), the entire contents and disclosure of which is hereby incorporated by reference. Also, the entire phage T4 genome could be replaced with multiple copies of concatemeric foreign DNA construct. By incubating these genetically modified T4 bacteriophages with, for example, fusion proteins comprising Hoc/Soc fused to the HIV antigen nef in the in vitro assembly system of the present invention, one could create a novel T4 bacteriophage that comprises DNA encoding a particular antigen inside and the corresponding antigen displayed outside on the capsid surface. As would be appreciated by those skilled in the art, a number of combinations of this embodiment, including multiple genes cloned inside and expressed outside can be envisioned.

In yet another embodiment, it may be possible to use a T4 bacteriophage of the present invention to accomplish further modulation of immune responses. For example, one may incorporate various inflammatory mediators onto the T4 bacteriophage platform that amplify the immune response. Such inflammatory mediators include, but are not limited to, various cytokines such as interleukins, lymphokines, tumor necrosis factor, and interferons, as well as other inflammatory mediators such as chemokines. Utilizing the in vitro assembly system of the present invention, one may display these inflammatory mediators, either full-length or the functional motifs and domains, on the T4 bacteriophage surface, or, in other embodiments, one may incorporate DNA constructs encoding inflammatory mediators into the genome of the T4 bacteriophage.

Another embodiment of the present invention comprises customized T4 bacteriophages that are devoid of packaged DNA. For example, by manipulating T4 genetics (eg., packaging-defective mutations in genes 16 and 17) through methods known to those of skill in the art, it may be possible to produce hoc⁻ and/or soc⁻ T4 bacteriophage mutants that are devoid of packaged DNA as described in Rao, V. B., and Black, L. W., "DNA packaging of bacteriophage T4 proheads in vitro: Evidence that prohead expansion is not coupled to DNA packaging" in *J. Mol. Biol.*, 185: 565-578 (1985).

Using the in vitro loading system of the present invention, it may be possible to then load Hoc and/or Soc fusion proteins onto the hoc⁻ and/or soc⁻ T4 bacteriophage mutants to create T4 bacteriophages that are devoid of DNA. It may be possible to use the T4 bacteriophages of this embodiment as an alternative to DNA-containing T4 bacteriophages when the presence of DNA is a biosafety concern. And because this embodiment does not affect the molecular constituents of the T4 bacteriophage capsid surface, it may be possible to use this strategy in combination with many of the embodiments disclosed herein.

In another embodiment of the present invention comprises, the customized T4 bacteriophages bound to a substrate may comprise a mixture of various T4 bacteriophages. In this embodiment, it may be possible to mix T4 bacteriophages according to any of the embodiments described herein with other, different T4 bacteriophages of the present invention. For example, a vaccine composition against both anthrax and HIV may comprise an HIV-antigen displayed separately on one set of T4 bacteriophages and an anthrax antigen displayed separately on another set of T4 bacteriophages, with each set of nanoparticles created using the in vitro assembly system of the present invention. Using this approach, one could, for example, create a single multicomponent vaccine formulation against a variety of infections different diseases.

In another embodiment, the T4 bacteriophage system of the present invention can also be developed as a unique molecular diagnostic system by exploiting the displayed molecules to detect pathogens/components through specific interactions.

In another embodiment, the displayed antigens on a customized bacteriophage may generate additional (synergestic) responses such as antitoxin effects plus immune responses. For instance, the displayed antigens can serve as antitoxins as well as efficacious vaccines at the same time. In the case of an anthrax spore attack, antibiotic treatment as well as vaccine administration are necessary. The immediate use of antibiotic will inhibit (eliminate) the progress of the on-going *B. anthracis* bacterial infection. But, a fraction of the spores can remain in the body for weeks (or months) and cause subsequent infection(s). Thus, vaccination is also necessary in order to neutralize the latter infection. Immunization with phage T4 displaying an antitoxin(s), for instance the PA63-binding N-terminal domain of LF and/or EF, the toxic effects of the initial infection can be neutralized immediately by interfering with the formation of lethal toxin and edema toxin. High density display of the domain (810 copies per capsid in the case of Soc-LF domain fusion) will serve as a polyvalent toxin inhibitor, thus greatly enhancing the affinity to bind to PA63 and neutralize the toxin formation as described in Nourez, M., Kane, R. S., Mogridge, J., Metallo, S., Deschatelets, P., Sellman, B. R., Whitesides, G. M. and Collier, R. J., "Designing a polyvalent inhibitor of anthrax toxin" in *Nature Biotechnology*, 19, 958-961 (2001), the entire contents and disclosure of which is hereby incorporated by reference. The same T4 particles alone, or in combination with an additional T4 bacteriophage (eg., PA-Hoc-T4), administered at the same time, will also serve as a vaccine generating neutralization immune responses and eliminate subsequent infection resulting from delayed spore germination.

There are essentially there are no significant size limitations with respect the size of the antigen that may be displayed on a T4 bacteriophage component. So far, very large antigens up to the size of 93 kDa or large hetero-oligomeric complexes up to 700 kDa can be displayed on phage T4 as described in Li, Q., Shivachandra, S. B., Zhang, Z. and Rao, V. B., "Assembly of the Small, Outer Capsid protein, Soc, on bacteriophage T4: a novel system for high density display of multiple large anthrax toxins and foreign proteins on phage capsid" in *J. Mol. Biol*, 370:1006-1019 (2007) and Fokine, A., Bowman, V. D., Battisti, A. J., Li, Q., Chipman, P. R., Rao, V. B. and Rossmann, M. G., "Cryo-electron microscopy study of bacteriophage T4 displaying anthrax toxin proteins" in *Virology*, 367:422-427 (2007), the entire contents and disclosures of which are hereby incorporated by reference.

EXAMPLES

The description of the present invention is enhanced by the various examples that follow.

Example 1

Figure 6:
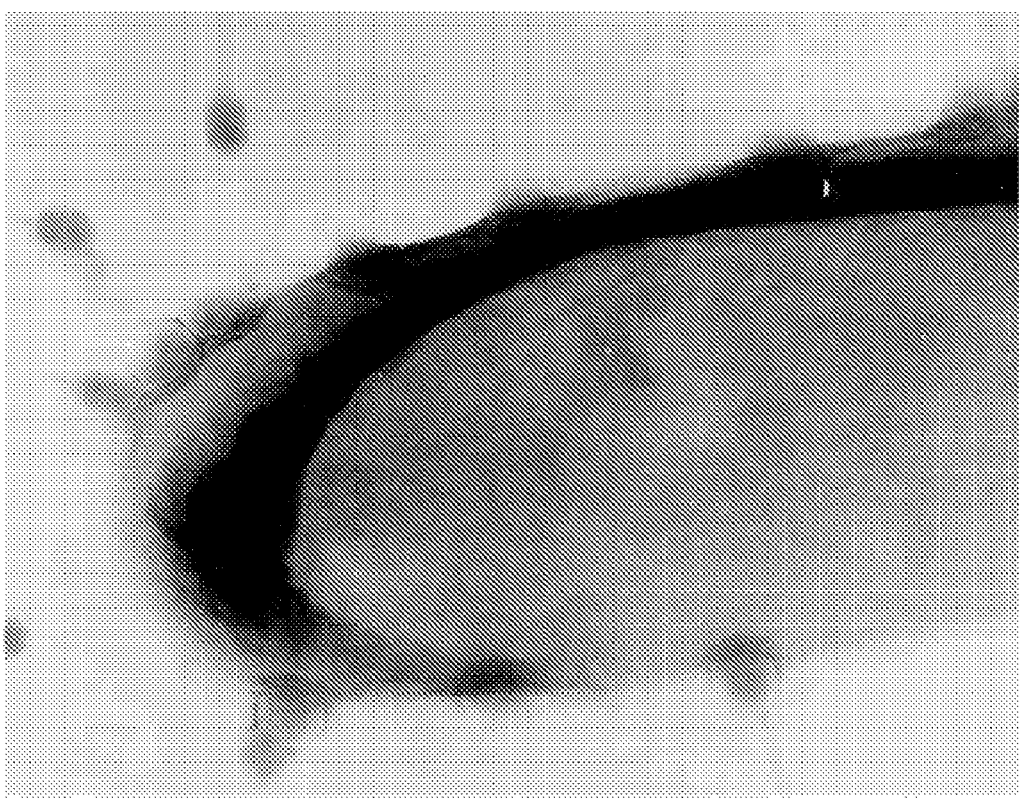
FIG. 6 is an electron micrograph of liposomes containing glucosyl ceramide and bound T4 bacteriophage in accordance with one embodiment of the present invention.

Liposomes containing glucosyl ceramide and bound T4 bacteriophage are made in accordance with one embodiment of the present invention. FIG. 6 is an electron micrograph of the liposomes.

Example 2

Figure 7:
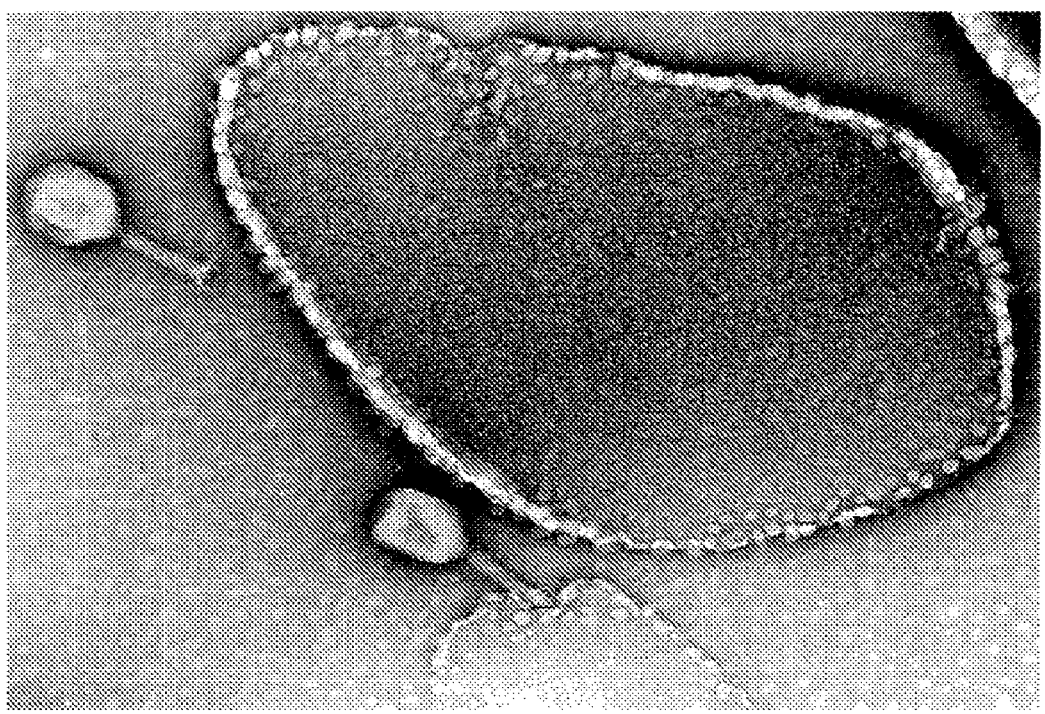
FIG. 7, is an electron micrograph of a large multilamellar liposome in accordance with one embodiment of the present invention.

Large multilamellar liposomes are made in accordance with one embodiment of the present invention. FIG. 7 is an electron micrograph of one of these liposomes.

Example 3

Figure 8:
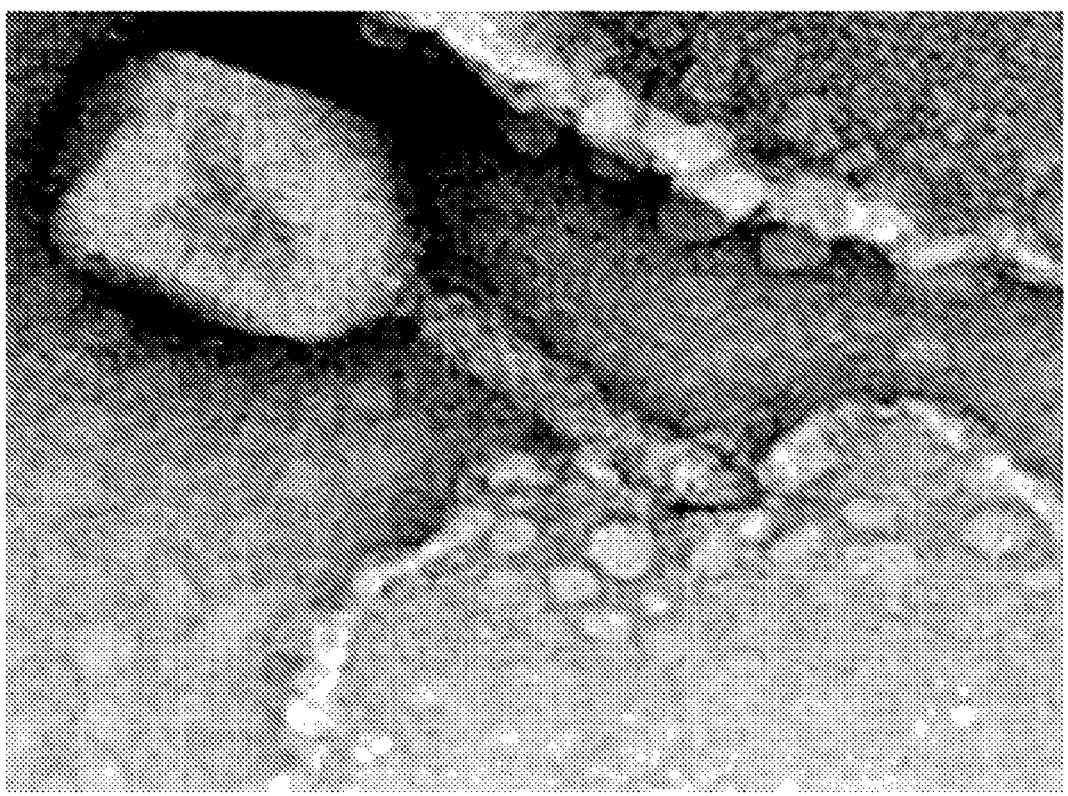
FIG. 8 is an electron micrograph of a large multilamellar liposome having a bacteriophage T4 in accordance with one embodiment of the present invention.

A T4 bacteriophage is bound to a large multilamellar liposome of Example 2 to form a complex. FIG. 8 is an electron micrograph of the complex.

Example 4

Figure 11:
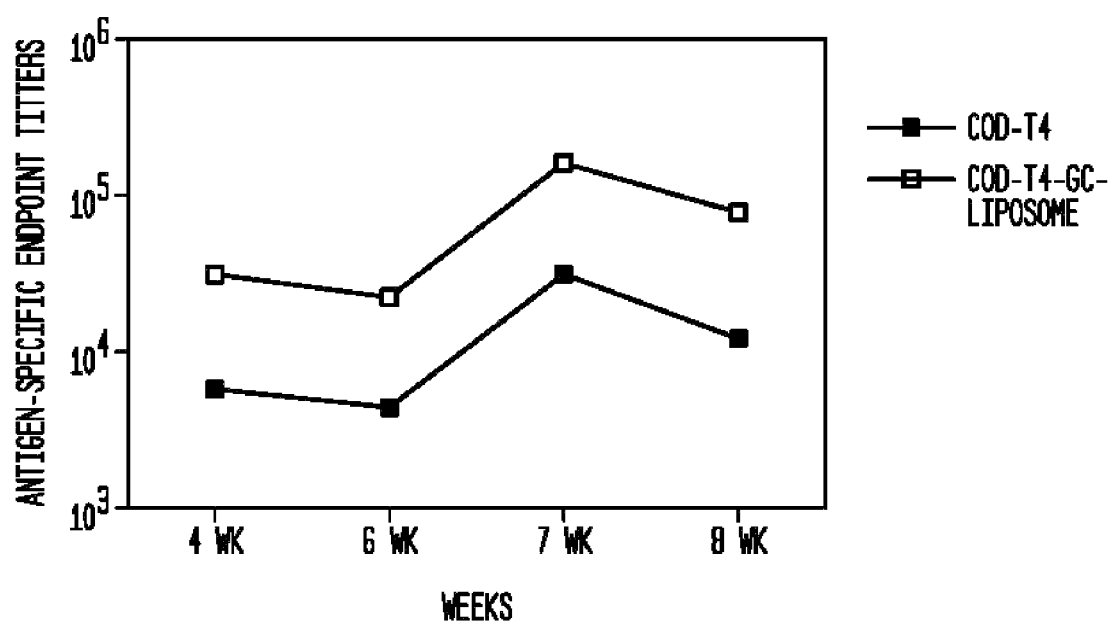
FIG. 11 is a graph of the immunogenicity of T4-bacteriophage-liposome-glycolipid complexes.

Several different formulations of liposomes containing glucocerebroside are prepared to capture the nanoparticle T4 bacteriophage displaying HIV antigen and loaded with DNA. In addition, HIV envelope antigens are incorporated into the liposomes binding the nanoparticles. The liposome-T4 formulations should elicit strong immune responses as shown by the graph of FIG. 11.

Example 5

Fluorescent-Labeled T4. T4 bacteriophages are labeled with fluorescent dyes. Procedures used previously for labeling dengue virus, attenuated yellow fever virus and irradiated Ebola virus with Alexa Fluor® dyes are used for labeling T4 (see below). The retention of infectivity of labeled T4 is confirmed by in vitro plaque assays. Fluorescent-labeled T4 are placed in binding assays with multilamellar or microfluidized unilamellar liposomes engineered with various concentrations of glycolipids (glucocerebroside, galactocerebroside, and lactocerebroside).

It is anticipated that glycolipids will serve as receptors for phage T4 attachment and thus provide binding specificity. The liposomes will also contain the potent adjuvant lipid A. Varying concentrations of labeled T4 are incubated with each of the liposome formulations. Unbound phage are removed by low speed centrifugation. The pellet will contain T4 bound to liposomes. Quantitative data for the binding of glycolipid containing liposomes to T4 are obtained using flow cytometry, ELISA, and Biacore analysis. Direct interaction between glycolipid containing liposomes and T4 are visualized by electron microscopy after negative staining with phosphotungstic acid.

Example 6

HIV Envelope Proteins and Liposomal Formulations. The intracellular trafficking of the antigen-T4-glycolipid-liposome complex in antigen-presenting cells (primary as well as cell lines) is examined using confocal fluorescence microscopy. The immunogenicity of the complexes are evaluated in mice and rabbits. The displayed antigens will include HIV envelope proteins.

Neutralizing antibodies are evaluated by two assays that are widely used in the HIV-1 field. The first assay is the PBMC assay described in Brown B. K., Darden, J. M., Tovanabutra, S., Oblander, T., Frost, J., Sanders-Buell, E., deSouza, M. S., Birx, D. L., McCutchan, F. E., and Polonis, V. R., "Biologic and genetic characterization f a panel of 60 human immunodeficiency virus type 1 isolate, representing clades A, B, C, D, CRF01_AE, and CRF02_AG, for the development and assessment of candidate vaccines" in *Journal of Virology,* 79:6089-6101 (2005); Brown, B. K., Karasavvas, N., Beck, Z., Matyas, G. R., Birx, D. L., Polonis, V. R., and Alving, C. R., "Monoclonal antibodies to phosphatidylinositol phosphate neutralize human immunodeficiency virus type 1: role of phosphate-binding subsites" in *Journal of Virology,* 81:2087-2091 (2007), the entire contents and disclosure of which is hereby incorporated by reference. Briefly, in this assay, the serum or plasma sample is incubated with a predetermined HIV virus dilution and then phytohemagglutinin stimulated PBMCs from HIV-1 negative donors are added. After an overnight incubation, the cells are added and recultured for 4 to 6 days. The amount of p24 present in the culture supernatant is determined by a p24 capture ELISA. The second assay is the TZM-bl pseudovirus assay described in Binley, J. M. et al., "Comprehensive cross-clade neutralization analysis of a panel of anti-human immunodeficiency virus type 1 monoclonal antibodies" in *Journal of Virology,* 78:13232-13252 (2004); Brown, B. K., Karasavvas, N., Beck, Z., Matyas, G. R., Birx, D. L., Polonis, V. R., and Alving, C. R., "Monoclonal antibodies to phosphatidylinositol phosphate neutralize human immunodeficiency virus type 1: role of phosphate-binding subsites" in *Journal of Virology,* 81:2087-2091 (2007), the entire contents and disclosures of which are hereby incorporated by reference. TZM-bl (also known as JC-53BL) is a HeLa cell line. In this assay, the cloned HIV-1 envelope genes are co-transfected with a defective HIV-1 genome backbone (SG3) to generate viral particles capable of a single round of infection in target cells and luciferase is the readout in this assay. Total antibody, cellular and mucosal immune responses are evaluated including antigen specific-ELISA, ELISPOT, intracellular cytokine staining, lymphocyte proliferation and cytotoxic T-cell assays to determine the scope of the immune response against these nanoparticle complexes.

Example 7

Antigen binding to T4. HIV proteins are bound to T4 bacteriophage capsids using methods similar to described in U.S. Patent Application No. 2005/0226892 to Rao, entitled "Methods and compositions comprising bacteriophage nanoparticles," filed Oct. 3, 2005, the entire contents and disclosure of which is hereby incorporated by reference Example 8

Preparation of liposomes. The multilamellar WRAIR liposomes (DMPC: DMPG: Cholesterol with Lipid A) containing various concentrations (0-150 μg/μmole of phospholipid) of glycolipids (glucocerebroside, galactocerebroside, and lactocerebroside) are prepared by standard methods described in Wassef, N. M., Alving, C. R., Richards, R. L., "Liposomes as carriers for vaccines" in *Immuno. Methods,* 4, 217-222 (1994), the entire contents and disclosure of which is hereby incorporated by reference. Once the optimal formulation is determined, a fluorescent lipid is added to the liposomes as a marker. Unilamellar liposomes are prepared using a microfluidizer.

Example 9

Fluorescent labeling of bacteriophage T4. Successful labeling of dengue virus, attenuated yellow fever virus and irradiated Ebola virus with Alexa® Fluor dyes has been achieved, and shown that the labeled dengue virus retained its infectivity described in (Palmer, D. R., Fernandez, S., Bisbing, J., Peachman, K. K., Rao, M., Darvir, D. Gunther, V., Burgess, T., Kono, Y., Padmanabhan, R., and Sun, W., "Restricted replication and lysosomal trafficking of Yellow Fever 17D vaccine virus in human dendritic cells" in *J. Gen. Virol*. January; 88 (Pt 1):148-56 (2007) and Peachman, K. K., Rao, M., Alving, C. R., Palmer, D. R., Sun, W. and Rothwell, S. W., "Human Dendritic Cells and Macrophages Exhibit Different Intracellular Processing Pathways for Soluble and Liposome-Encapsulated Antigens" in *Immunobioloy,*

210:321-333 (2005), the entire contents and disclosures of which are hereby incorporated by reference. Similar procedures are used for labeling bacteriophage T4 ($1 \times 10^{10}$ pfu) with Alexa® Fluor 488 or 594 (Molecular Probes, Eugene, Oreg.). To confirm infectivity of T4 bacteriophage labeled virus, plaque assays of labeled phage are performed.

Example 10

Determination of bacteriophage T4 binding to liposomes. Varying concentrations of labeled T4 bacteriophage are incubated with each of the liposome formulations in a total volume of 100 µl. Incubation is carried out at room temperature or at 37° C. for 1 hour. Unbound phage is removed by low speed centrifugation. T4 bound to liposomes will pellet and the supernatant will contain unbound virus and very small liposomes. Quantitative data for the binding of glycolipid containing fluorescent liposomes to fluorescent phage T4 is obtained using flow cytometry.

Additionally, surface plasmon resonance is employed using a Biacore 2000 to look at T4-liposome interactions to determine binding affinities including $K_a$ and $K_d$ values. Two different Biacore chips, L1 and CM5, is used to covalently attach either glycolipid continuing liposomes or phage T4 displaying HIV-1 antigens. Binding of phage T4 to unilamellar liposomes is determined by surface plasmon resonance.

Example 11

Electron Microscopy. Direct interaction between glycolipid containing liposomes and phage T4 is visualized by electron microscopy. The preparations are visualized after negative staining with phosphotungstic acid.

Example 12

Evaluation of the immunogenicity of the liposome-T4-antigen complex. The immunogenicity of the liposome-T4-antigen (HIV protein and/or DNA) complex is evaluated first in mice and then in rabbits. Female BALB/c mice or rabbits are immunized on weeks 0, 3, and 6. Animals are bled every two weeks and individual serum samples are analyzed for Env-specific and T4 Hoc-specific IgG antibodies by ELISA. Mucosal immune responses are assessed by measuring the IgA levels in the serum and vaginal washes. Rabbits are evaluated for humoral immunity only. One week after the last boost, mice are euthanized and spleens and lymph nodes from naïve and immunized mice are isolated. Single cells suspensions are made and tested for Env specific cellular immune responses. T cell proliferation in spleen and lymph node cells are measured by CFSE labeling using a flow cytometer. Antigen-specific cytokine (IFN-γ, IL-2, IL-4) producing cells are measured by ELISPOT assays described in Rao M, Bray M, Alving C R, Jahrling P, Matyas G R, "Induction of immune responses in mice and monkeys to Ebola virus after immunization with liposome-encapsulated irradiated Ebola virus: protection in mice requires CD4(+) T cells: in *J. Virol.* September; 76 (18):9176-85 (2002). Intracellular cytokine staining (IFN-γ, IL-2, IL-4, IL-10, IL-12) are measured by flow cytometry. Generation of cytotoxic T cells are measured by the standard chromium release assay as described in Rao, M., Matyas, G. M., Vancott, T. C., Birx, D. L. and Alving, C. R., *Immunology and Cell Biology* 82: 523-530 (2004), the entire contents and disclosure of which is hereby incorporated by reference.

Example 13

Liposome formulations containing glycolipids that achieve high T4 bacteriophage binding Liposome formulations containing glycolipids that achieve high T4 bacteriophage binding are made by the following method. Glucosyl ceramide 150 µg/µmol of phospholipids dissolved in a 9:1 chloroform:methanol mixture is combined with dimyristoyl phosphatidylcholine (DMPC), dimyristoyl phosphatidylglycerol (DMPG), cholesterol (Avanti Polar lipids, Alabaster, Ala.) in molar ratios of 1.8:0:2:1.5 each dissolved separately in chloroform. The solvent dissolved lipids are mixed together and the solvent is removed by rotary evaporation. The dried lipids are placed under high vacuum to remove the residual solvent. The dried lipids are then dispersed in water before being lyophilized. The lyophilized lipids are dispersed in either phosphate buffered saline or Tris buffered saline before combining with the T4 bacteriophage. Liposomes with various concentrations of glucosyl ceramide (0, 50, 100, and 150 µg/µmol of phospholipids) were prepared and binding to T4 bacteriophage was determined. The optimum concentration of glucosyl ceramide to achieve maximum binding of phage T4 is 150 µg/µmol of phospholipids. Substituting galactosyl ceramide for glucosyl ceramide in the above description, results in a poor T4 bacteriophage binding-liposome formulation. In contrast, substituting lipid A (a non-glycolipid) at 10 µg/ml, List Biological Laboratories, Inc., Campbell, Calif. for the glycosyl ceramide in the above description also constitutes a high T4 bacteriophage binding liposome formulation. The present example makes use of information in the following works: Alving, C. R., Shichijo, S., Mattsby-Baltzer, I., Richards, R. L., Wassef, N. M., "Preparations and use of liposomes in immunological studies" In *Liposome Technology*: G. Gregoriadis, ed., CRC Press Inc., Boca Raton, Fla., Vol. 3, p. 317-343 (1993) and Wassef, N. M., Alving, C. R., Richards, R. L., "Liposomes as carriers for vaccines" in *Immuno. Methods* 4, 217-222 (1994), the entire contents and disclosures of which are hereby incorporated by reference.

Example 14

Characterizing T4 bacteriophage—liposome-glycolipid binding properties. T4 bacteriophage—liposome-glycolipid binding properties are characterized by two methods; (i) direct visualization of the T4 bacteriophage-liposome complex by negative staining under an electron microscopy, and (ii) binding of bacteriophage T4 to liposomes measured in real time by surface plasmon resonance.

Figure 9:
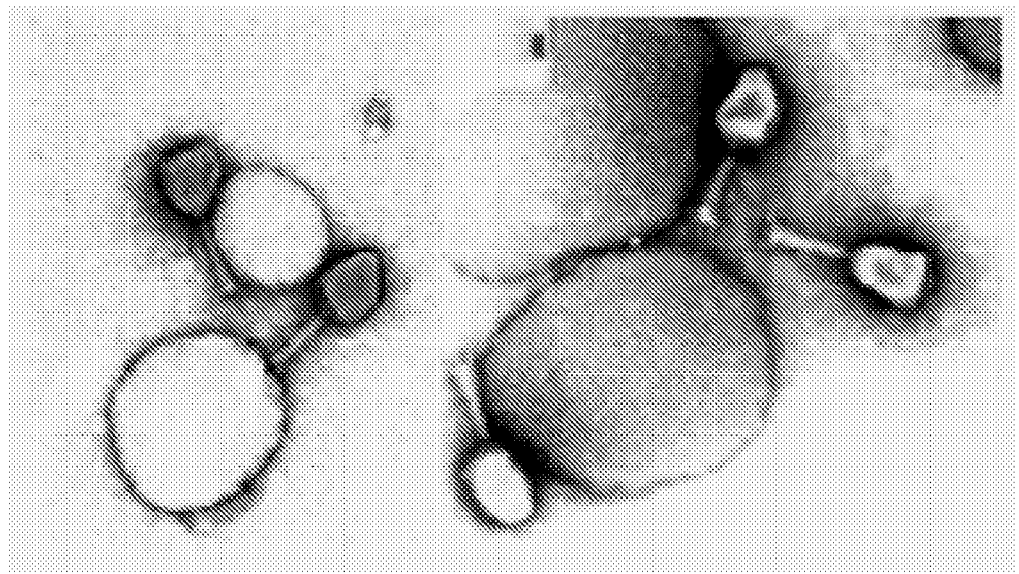
FIG. 9 is an electronmicograph of a sample of liposomes containing glucosyl ceramide incubated with wild type T4 bacteriophages.
Figure 10:
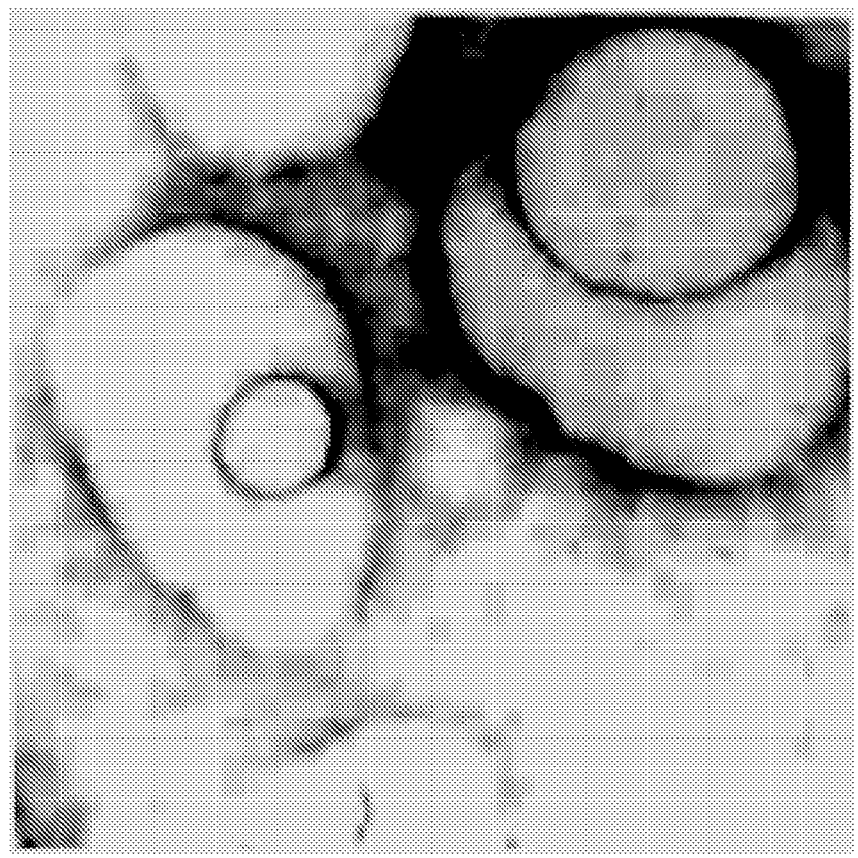
FIG. 10 is an electronmicograph of a sample of liposomes lacking glucosyl ceramide incubated with wild type T4 bacteriophages.

Electron microscopy is preformed by the following method. Wild-type T4 bacteriophage ($1 \times 10^{10}$) particles are mixed with 50 µL of 50 mM phospholipid containing liposomes with and without glucosyl ceramide (150 µg/µmol of phospholipid) for 1 hr at room temperature and then washed by centrifugation for 10 min at 7,000 rpm at 4° C. in 7.5 mL of saline to remove the unbound phage. The pellet of bacteriophage T4-liposome complex is negatively stained for 10 min with either 2% phosphotungstic acid or with 1% uranyl acetate for 30 sec. The pellet is gently washed and then examined under a Zeis 912AB electron microscope. The electron microscopist is handed blinded samples for evaluation. Samples containing liposomes with the glycolipid glucosyl ceramide contain the most T4 bacteriophage—liposome-glycolipid complexes (FIG. 9) whereas, samples lacking glucosyl ceramide have few to no complexes (FIG. 10). For the sample in FIG. 9 bacteriophage T4 was incubated with liposomes containing glucosyl ceramide (150 µg/µmol of phospholipids). For FIG. 10 the same amount of bacteriophage T4 was incubated liposomes lacking glucosyl ceramide. Samples were negatively stained with 1% uranyl acetate.

Figure 4:
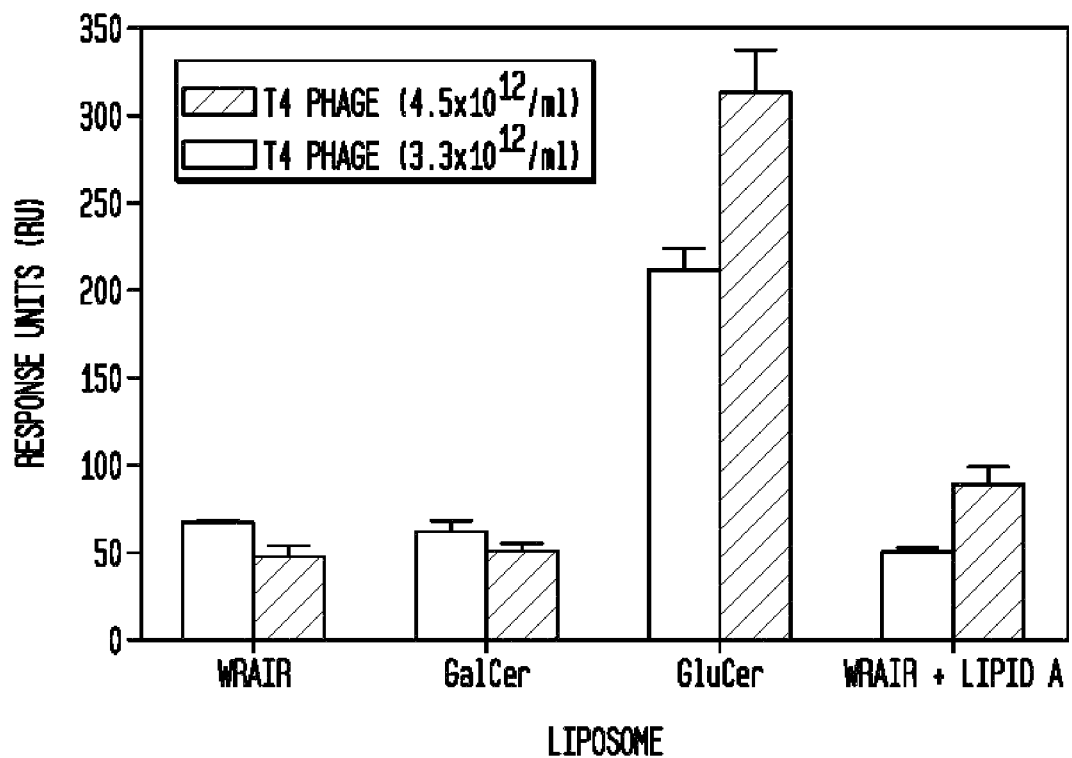
FIG. 4 is a graph showing binding of phage T4 to glucocerebroside containing liposomes.

T4 bacteriophage-liposome-glycolipid binding as measured by surface plasmon resonance utilizing a Biacore 2000 instrument. Liposomes are prepared as described above in Example 13. Liposomes either lack or contain lipid A or 150 µg of galactocerebroside (GalCer) or 150 µg of glucocerebroside (GluCer). The liposome preparation contains multilamellar vesicles ranging in size from a 0.1 micron to 100 microns. To get a uniform preparation of liposomes with a single size and to prevent the clogging of the pores in the Biocore machine, unilamellar liposomes are prepared by passing the multilamellar liposomes through multiple rounds of extrusion using decreasingly smaller filters until the liposome population is uniform at 0.1 to 0.15 micron as confirmed by a particle sizer. Each of the preparations of the unilamellar liposomes are injected as a 500 mM suspension of phospholipid, until 4000 Response Units (RU, arbitrary units) is captured on individual flow cells of a Biacore L1 sensor chip. The lipid surface is washed with Hanks Balance Salt Solution (HBS) to remove unbound liposomes. Wild-type bacteriophage T4 (90 µl), ranging in concentration from $3.52 \times 10^{10}$ virions/ml to $4.5 \times 10^{12}$ virions/ml or phosphate buffered saline (negative control) is injected over the captured liposome surface at a flow rate of 30 µl/min. Binding is allowed to proceed for 180 seconds and dissociation is observed for 480 seconds. Data points are collected 30 seconds after the end of the injection. The response units obtained with the negative control are subtracted from the T4 binding data. The bar graph of FIG. 4 represents the mean response units of three experiments ±S.D.

In FIG. 11 serum levels of gp41-specific IgG endpoint titers in BALB/c mice are shown. Open squares represent gp41-specific IgG end point titers from mice immunized with the HIV antigen cytoplasmic domain-Hoc fusion protein displayed on T4 bacteriophage with liposomes containing glucosyl ceramide and lipid A. Filled squares represent mice immunized with cytoplasmic domain-Hoc fusion protein displayed on T4 bacteriophage in the absence of any liposomes. Individual serum samples are analyzed in each case at weeks 4, 6, 7, and 8, respectively and the value is represented as the geometric mean.

Although bacteriophage T4 binds to liposomes containing lipid A, the binding is 3-fold higher with liposomes containing glucosyl ceramide. A dose dependent increase in binding is observed as the number of phage particles is increased.

Example 15

T4 bacteriophage-liposome-glycolipid complexes are highly immunogenic when used in the following vaccine formulation which includes the cytoplasmic outer domain (COD) of HIV-1 envelope protein gp41 fused to Hoc and displayed on T4 bacteriophage (2 µg of protein per $1.44 \times 10^{12}$ phage) either in the presence or absence of glucosyl ceramide (150 µg/µmol of phospholipids) and lipid A (10 µg) containing liposomes. Intramuscular immunization of BALB/c mice by the intramuscular route at 0, 3 and 6 weeks with these formulations results in gp41-specific serum IgG antibody responses as measured at 4, 6, 7 and 8 weeks using an enzyme linked immunosorbent method (ELISA) as previously described by Rao, M., Matyas, G. M., Vancott, T. C., Birx, D. L. and Alving, C. R, "Immunostimulatory CpG motifs induce cytotoxic T lymphocyte responses to human immunodeficiency virus type I oligomeric gp140 envelope protein" in *Immunology and Cell Biology*, 82: 523-530 (2004), the entire contents and disclosure of which is hereby incorporated by reference, and using full-length gp41 as the coating antigen in the ELISA assay. Mice immunized with the COD-T4 bacteriophage-liposome-glycolipid complex that contain lipid A and glucosyl ceramide induced higher antigen-specific IgG antibody titers (at least one log higher) than mice immunized with COD-T4 in the absence of glucosyl ceramide and lipid A containing liposomes. This result was consistent at all the time points tested, see FIG. 11.

FIG. 11 shows serum levels of gp41-specific IgG endpoint titers in BALB/c mice. Open squares represent gp41-specific IgG end point titers from mice immunized with the HIV antigen cytoplasmic domain-Hoc fusion protein displayed on T4 bacteriophage with liposomes containing glucosyl ceramide and lipid A. Closed squares represent mice immunized with cytoplasmic domain-Hoc fusion protein displayed on T4 bacteriophage in the absence of any liposomes. Individual serum samples are analyzed in each case at weeks 4, 6, 7, and 8, respectively and the value is represented as the geometric mean.

Example 16

Preliminary data suggests that binding to unilamellar liposomes is higher than to the multilamellar liposomes. Multilamellar liposomes are made as described in Example 13. Unilamellar liposomes are prepared as described in Example 14. T4 bacteriophage displaying C-trimer-Hoc protein, a trimeric sequence of the HIV envelope protein, are incubated with either multilamellar liposomes or with unilamellar liposomes as described above in Example 13 and Example 14, for 1 hour at room temperature. The construction of the trimeric recombinant was described in Sathaliyawala, T., Rao, M., Maclean, D. M., Birx, D. L., Alving, C. R. and Rao, V. B., "Assembly of Human Immunodeficiency Virus (HIV) antigens on Bacteriophage T4: a Novel In vitro Approach To Construct Multicomponent HIV Vaccines. *J. Virology*, 80: 7688-7698 (2006), the entire contents and disclosure of which is hereby incorporated by reference. The complex is washed to remove unbound bacteriophage T4 and both preparations are examined under an electron microscope after negative staining as described above. The results show more phage-liposome complexes per field examined with unilamellar liposomes.

Figure 12:
FIG. 12 is an electron micrograph of T4 bacteriophages displaying HIV-C-Trimer-Hoc fusion protein binding to unilamellar liposomes.
Figure 13:
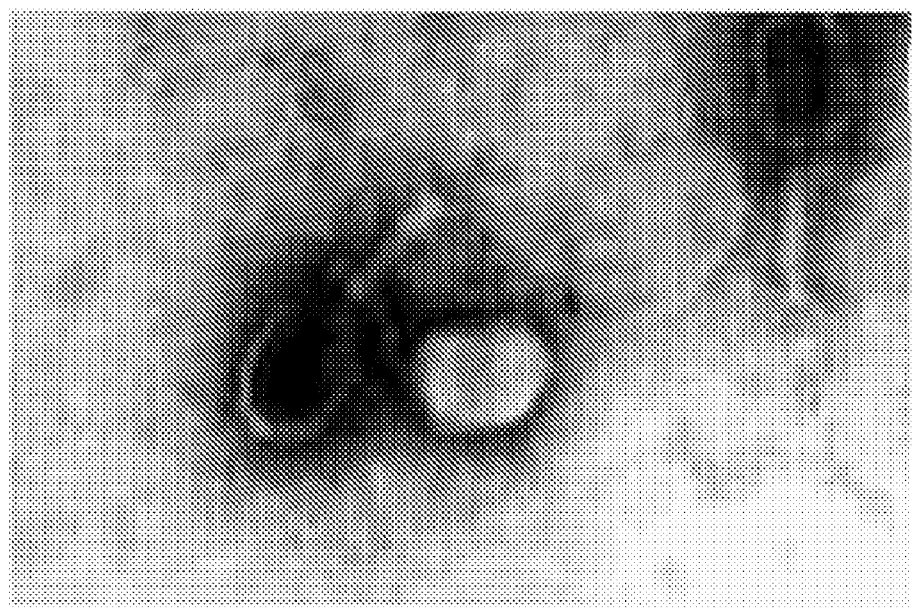
FIG. 13 is an electron micrograph of T4 bacteriophages displaying HIV-C-Trimer-Hoc fusion protein binding to unilamellar liposomes.

FIGS. 12 and 13 show T4 bacteriophage displaying HIV-C-Trimer-Hoc fusion protein binding to unilamellar liposomes containing glucosyl ceramide.

Example 17

Examining the binding characteristics of liposomes containing HIV envelope proteins and T4. Liposome formulations containing glycolipids that achieve high T4 bacteriophage binding are made as described above in Example 13. The binding characteristics of wild-type T4 bacteriophage and T4 bacteriophage displaying C-trimer HIV-1 envelope proteins is measured by surface plasmon resonance on a Biacore 2000. Unilamellar liposomes with or without glucosyl ceramide are immobilized on a L1 chip. $5 \times 10^{12}$ T4 bacteriophage particles either displaying or not displaying C-trimer gp41 HIV antigen are passed over the captured liposomes. Binding is measured on the Biacore 2000 as response units. The highest level of binding (1250 RU) is obtained when T4 bacteriophage C-trimer gp41 HIV-antigen is complexed with glucosyl ceramide containing liposomes. Wild-type T4 lacking the C-trimer antigen also binds to glucosyl ceramide containing liposomes (500 RU). Wild-type T4 bacteriophage and T4 bacteriophage displaying HIV C-trimer envelope protein bind poorly to liposomes lacking glucosyl ceramide (100 RU).

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

What is claimed is:

1. A composition comprising a substrate, wherein the substrate comprises a liposome and a glucoconjugate; and one or more T4 bacteriophage or T4 bacteriophage derivative thereof that is bound to the substrate by the glucoconjugate, wherein the glucoconjugate is a glucosyl ceramid inserted into the lipid bilayer of the liposome and wherein the T4 bacteriophage derivate is T4 bacteriophage having antigens, fusion proteins or other types of molecule attached thereof.

2. The composition of claim 1, wherein the substrate comprises an adjuvant.

3. The composition of claim 1, wherein there are one or more types of antigens bound to one or more T4 bacteriophage.

4. The composition of claim 1, wherein there are two or more different types of antigens bound to one or more T4 bacteriophage.

5. The composition of claim 3, wherein the one or more types of antigens bound to one or more T4 bacteriophage.

6. The composition of claim 1, wherein there are Hoc and/or Soc fusion proteins bound to one or more T4 bacteriophage.

7. The composition of claim 6, wherein each of the fusion protein comprised of a foreign protein fused to a Hoc or Soc protein or fragment thereof.

8. The composition of claim 7, wherein each foreign protein is antigenic.

9. The composition of claim 7, wherein the foreign protein is selected from the group consisting of: an interleukin, phospholipase A2, endotoxin, staphylococcal enterotoxin B, Type I Interferon, Type II Interferon, Tumor Necrosis Factor (TNF-a or b), Transforming Growth Factor-β ("TGF-β"), Lymphotoxin, Migration Inhibition Factor, Granulocyte-Macrophage Colony-Stimulating Factor ("CSF"), Monocyte-Macrophage CSF, Granulocyte CSF, vascular epithelial growth factor ("VEGF"), Angiogenin, transforming growth factor ("TGF-a"), heat shock protein, fibroblast growth factor, other inflammatory and immune regulatory protein, cancer cell specific antigen, MART, MAGE, BAGE, mutant p53, tyrosinase, mucine antigen, prostate specific antigen (PSA), TSH, autoimmune antigen, angeostatin, endostatin, vascular endothelial growth factor (VEGF), and a fragment thereof.

10. The composition of claim 1, wherein the liposome comprises lipid A.

11. The composition of claim 1, wherein the liposome comprises an adjuvant.

12. The composition of claim 1, wherein the liposome is a unilamellar liposome.

13. A composition comprising:
a substrate, wherein the substrate comprises a liposome and a glucoconjugate; and
one or T4 bacteriophage derivative thereof that are each bound to the substrate by the glucoconjugate, wherein the T4 bacteriophage derivate is T4 bacteriophage having antigens, fusion proteins or other types of molecule attached thereof,
wherein the glucoconjugate is a glycolipid inserted into the lipid bilayer of the liposome, and
wherein the liposome comprises dimyristoyl phosphatidylcholine, dimyristoyl phosphatidylglycerol, cholesterol and lipid A.

14. The composition of claim 13, wherein there are one or more types of antigens bound to one or more T4 bacteriophage.

15. The composition of claim 13, wherein there are two or more different types of antigens bound to one or more T4 bacteriophage.

16. The composition of claim 13, wherein there are Hoc and/or Soc fusion proteins bound to one or more T4 bacteriophage.

17. The composition of claim 16, wherein each fusion protein comprises a foreign protein fused to a Hoc or Soc protein or fragment thereof.

18. The composition of claim 17, wherein each foreign protein is antigenic.

19. The composition of claim 17, wherein the foreign protein is selected from the group consisting of: an interleukin, phospholipase A2, endotoxin, staphylococcal enterotoxin B, Type I Interferon, Type II Interferon, Tumor Necrosis Factor (TNF-a or b), Transforming Growth Factor-β ("TGF-β"), Lymphotoxin, Migration Inhibition Factor, Granulocyte-Macrophage Colony-Stimulating Factor ("CSF"), Monocyte-Macrophage CSF, Granulocyte CSF, vascular epithelial growth factor ("VEGF"), Angiogenin, transforming growth factor ("TGF-a"), heat shock protein, fibroblast growth factor, other inflammatory and immune regulatory protein, cancer cell specific antigen, MART, MAGE, BAGE, mutant p53, tyrosinase, mucine antigen, prostate specific antigen (PSA), TSH, autoimmune antigen, angeostatin, endostatin, vascular endothelial growth factor (VEGF), and a fragment thereof.

* * * * *